(12) United States Patent
Lifton et al.

(10) Patent No.: US 6,551,775 B1
(45) Date of Patent: Apr. 22, 2003

(54) METHOD TO DIAGNOSE AND TREAT PATHOLOGICAL CONDITIONS RESULTING FROM DEFICIENT ION TRANSPORT SUCH AS PSEUDOHYPOALDOSTERONISM TYPE-1

(75) Inventors: Richard P. Lifton, Guilford, CT (US); Sue S. Chang, Orange, CT (US); Bernard C. Rossier, Grandvaux (CH)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/380,836

(22) PCT Filed: Mar. 11, 1998

(86) PCT No.: PCT/US98/04681

§ 371 (c)(1),
(2), (4) Date: Apr. 27, 2000

(87) PCT Pub. No.: WO98/40516

PCT Pub. Date: Sep. 17, 1998

Related U.S. Application Data

(60) Provisional application No. 60/040,171, filed on Mar. 11, 1997.

(51) Int. Cl.[7] .......................... C12Q 1/68; C12P 19/34; C07H 21/04
(52) U.S. Cl. .................. 435/6; 435/91.2; 536/23.1; 536/24.33
(58) Field of Search .................. 435/6, 91.2; 536/23.1, 536/24.33

(56) References Cited

U.S. PATENT DOCUMENTS

| | | | |
|---|---|---|---|
| 5,683,872 A | * 11/1997 | Rudert et al. .................. | 435/6 |
| 5,693,756 A | 12/1997 | Li et al. ....................... | 530/350 |
| 5,798,265 A | * 8/1998 | Springer et al. ............. | 435/364 |
| 5,892,018 A | 4/1999 | Welsh et al. ................ | 536/23.5 |

OTHER PUBLICATIONS

EST database, Accession No. C01378, Okuba et al., Jul. 23, 1996.*

Canessa et al. (1993) "Epithelial sodium channel related to proteins involved in neurodegeneration" *Nature* 361: 467–470.

Canessa et al. (1994) "Amiloride–sensitive epithelial Na+ channel is made of three homologous subunits" *Nature* 367: 463–467.

Chang et al. (1996) "Mutations in subunits of the epithelial sodium channel cause salt wasting with hyperkalaemic acidosis, pseudohypoaldosteronism type 1" *Nature Genet.* 12, 248–253.

Grunder et al. (1996) "Cell and Transport Physiology: Inorganic Ions (Na, K, Cl)" *American Society of Nephrology* 29th Annual Meeting AO168.

Hansson et al. (1995) "A de novo missense mutation of the β subunit of the epithelial sodium channel causes hypertension and Liddle syndrome, identifying a proline–rich segment critical for regulation of channel activity" *Proc. Nat'l Acad. Sci. USA* 92: 11495–11499.

Hansson et al. (1995) "Hypertension caused by a truncated epithelial sodium channel γ subunit: genetic heterogeneity of Liddle syndrome" *Nature Genet.* 11, 76–82.

Schild et al. (1995) "A mutation in the epithelial sodium channel causing Liddle disease increases channel activity in the *Xenopus laevis* oocyte expression system" *Proc. Nat'l Acad. Sci. USA* 92: 5699–5703.

Shimkets et al. (1994) "Liddle's Syndrome: Heritable Human Hypertension Caused by Mutations in the β Subunit of the Epithelial Sodium Channel" *Cell* 79: 407–414.

Strautnieks et al. (1996) "Localisation of pseudohypoaldosteronism genes to chromosome 16p12.2–13.11 and 12p13.1–pter by homozygosity mapping" *Human Molecular Genetics* 5(2): 293–299.

Strautnieks et al. (1996) "A novel splice–site mutation in the γ subunit of the epithelial sodium channel gene in three pseudohypoaldosteronism type 1 families" *Nature Genetics* 13: 248–250.

Voilley et al. (1995) "Cloning, Chromosomal Localization, and Physical Linkage of the β and γ Subunits (SCNN1B and SCNN1G) of the Human Epithelial Amiloride–Sensitive Sodium Channel" *Genomics* 28: 560–565.

* cited by examiner

*Primary Examiner*—Stephanie Zitomer
(74) *Attorney, Agent, or Firm*—Morgan, Lewis & Bockius, LLP

(57) ABSTRACT

The present invention is based, in part, on the identification of the roles of the human ATP-sensitive K+ channel, ENaC in causing pathological condition associated with abnormal ion transport, particularly PHA1. The present invention specifically provides the amino acid sequence of several human altered variants of the ENaC protein as well as the nucleotide sequence that encodes these variants that can be used in diagnosing ion transport disorders.

6 Claims, 4 Drawing Sheets

Figure 1:
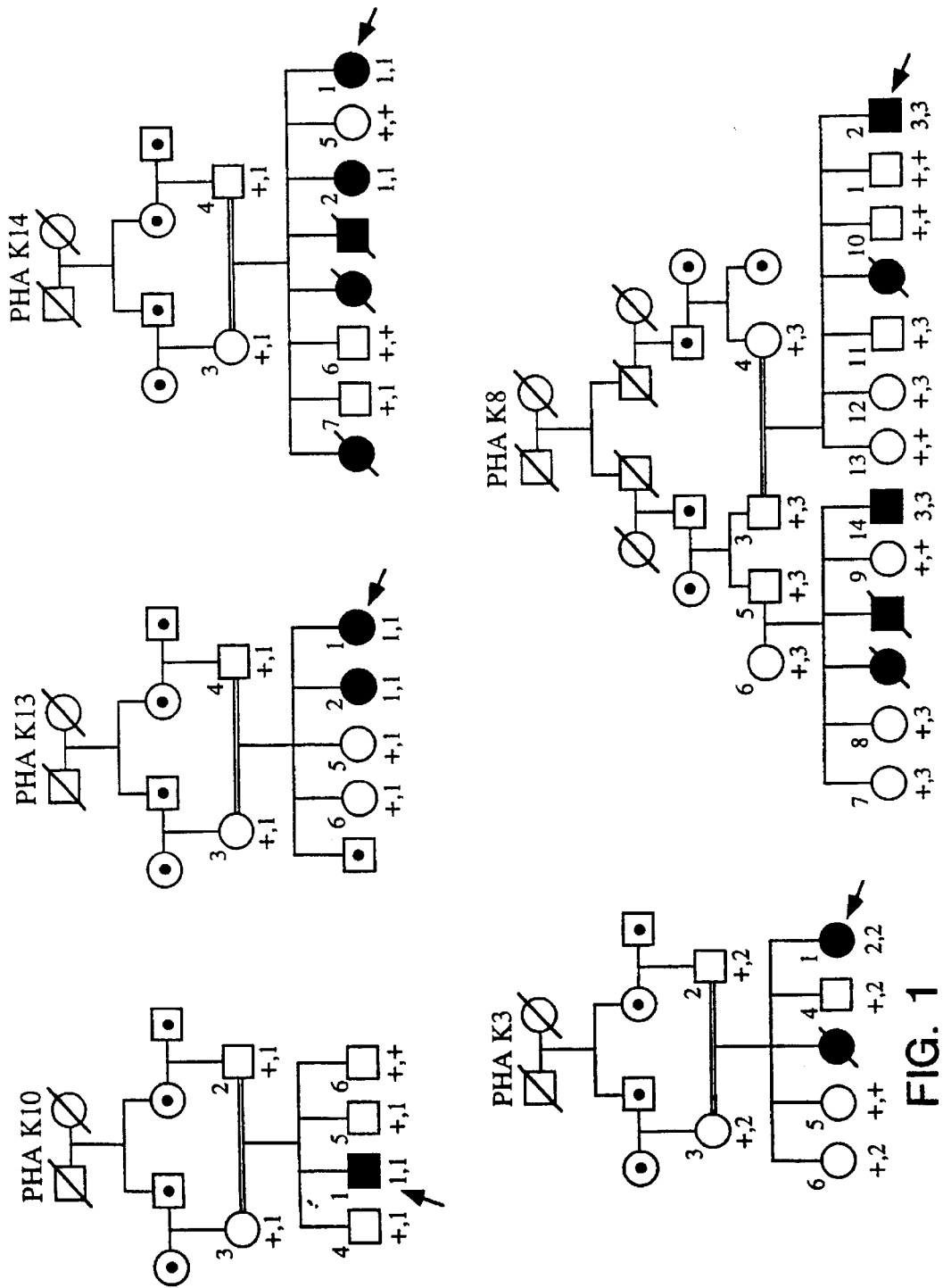

SEQUENCE LISTING

<160> NUMBER OF SEQ ID NOS: 106

<210> SEQ ID NO 1
<211> LENGTH: 13
<212> TYPE: DNA
<213> ORGANISM: Homo sapiens
<220> FEATURE:
<223> OTHER INFORMATION: Segment of wild-type alpha ENaC allele

<400> SEQUENCE: 1

```
ccaccatcca cgg                                                        13

<210> SEQ ID NO 2
<211> LENGTH: 11
<212> TYPE: DNA
<213> ORGANISM: Homo sapiens
<220> FEATURE:
<223> OTHER INFORMATION: Segment of mutant alpha ENaC allele

<400> SEQUENCE: 2
ccaccacacg g                                                          11

<210> SEQ ID NO 3
<211> LENGTH: 9
<212> TYPE: DNA
<213> ORGANISM: Homo sapiens
<220> FEATURE:
<223> OTHER INFORMATION: Segment of wild-type alpha ENaC allele

<400> SEQUENCE: 3 ctgtcgcga                                                              9

<210> SEQ ID NO 4
<211> LENGTH: 9
<212> TYPE: DNA
<213> ORGANISM: Homo sapiens
<220> FEATURE:
<223> OTHER INFORMATION: Segment of mutant alpha ENaC allele

<400> SEQUENCE: 4 ctgtcacga                                                              9

<210> SEQ ID NO 5
<211> LENGTH: 9
<212> TYPE: DNA
<213> ORGANISM: Homo sapiens
<220> FEATURE:
<223> OTHER INFORMATION: Segment of wild-type beta ENaC allele

<400> SEQUENCE: 5 cacggcccc                                                              9

<210> SEQ ID NO 6
<211> LENGTH: 9
<212> TYPE: DNA
<213> ORGANISM: Homo sapiens
<220> FEATURE:
<223> OTHER INFORMATION: Segment of mutant beta ENaC allele

<400> SEQUENCE: 6 cacagcccc                                                              9

<210> SEQ ID NO 7
<211> LENGTH: 11
<212> TYPE: PRT
<213> ORGANISM: Homo sapiens
<220> FEATURE:
<223> OTHER INFORMATION: Segment of beta ENaC protein

<400> SEQUENCE: 7

Cys Asp Asn Thr Asn Thr His Gly Pro Lys Arg
  1               5                  10

<210> SEQ ID NO 8
<211> LENGTH: 11
<212> TYPE: PRT
```

```
<213> ORGANISM: Rattus norvegicus
<220> FEATURE:
<223> OTHER INFORMATION: Segment of beta ENaC protein

<400> SEQUENCE: 8

Cys Asn Asn Thr Asn Thr His Gly Pro Lys Arg
  1               5                  10

<210> SEQ ID NO 9
<211> LENGTH: 11
<212> TYPE: PRT
<213> ORGANISM: Xenopus laevis
<220> FEATURE:
<223> OTHER INFORMATION: Segment of beta ENaC protein

<400> SEQUENCE: 9

Cys Asp Asn Thr Asn Thr His Gly Pro Lys Arg
  1               5                  10

<210> SEQ ID NO 10
<211> LENGTH: 11
<212> TYPE: PRT
<213> ORGANISM: Homo sapiens
<220> FEATURE:
<223> OTHER INFORMATION: Segment of human alpha ENaC protein

<400> SEQUENCE: 10

Cys Asn Asn Thr Thr Ile His Gly Ala Ile Arg
  1               5                  10

<210> SEQ ID NO 11
<211> LENGTH: 11
<212> TYPE: PRT
<213> ORGANISM: Rattus norvegicus
<220> FEATURE:
<223> OTHER INFORMATION: Segment of alpha ENaC protein

<400> SEQUENCE: 11

Cys Asn Asn Thr Thr Ile His Gly Ala Ile Arg
  1               5                  10

<210> SEQ ID NO 12
<211> LENGTH: 11
<212> TYPE: PRT
<213> ORGANISM: Xenopus laevis
<220> FEATURE:
<223> OTHER INFORMATION: Segment of alpha ENaC protein

<400> SEQUENCE: 12

Cys Ser Asn Thr Thr Ile His Gly Ala Ile Arg
  1               5                  10

<210> SEQ ID NO 13
<211> LENGTH: 11
<212> TYPE: PRT
<213> ORGANISM: Homo sapiens
<220> FEATURE:
<223> OTHER INFORMATION: Segment of gamma ENaC protein

<400> SEQUENCE: 13

Cys Leu Asn Thr Asn Thr His Gly Cys Arg Arg
  1               5                  10

<210> SEQ ID NO 14
<211> LENGTH: 11
<212> TYPE: PRT
<213> ORGANISM: Rattus norvegicus
```

```
<220> FEATURE:
<223> OTHER INFORMATION: Segment of gamma ENaC protein

<400> SEQUENCE: 14

Cys Met Asn Thr Asn Thr His Gly Cys Arg Arg
 1               5                  10

<210> SEQ ID NO 15
<211> LENGTH: 11
<212> TYPE: PRT
<213> ORGANISM: Xenopus laevis
<220> FEATURE:
<223> OTHER INFORMATION: Segment of gamma ENaC protein

<400> SEQUENCE: 15

Cys Leu Asn Thr Asn Thr His Gly Cys Arg Arg
 1               5                  10

<210> SEQ ID NO 16
<211> LENGTH: 11
<212> TYPE: PRT
<213> ORGANISM: Homo sapiens
<220> FEATURE:
<223> OTHER INFORMATION: Segment of delta ENaC protein

<400> SEQUENCE: 16

Cys Thr Asn Ala Ile Ile His Gly Ala Ile Arg
 1               5                  10

<210> SEQ ID NO 17
<211> LENGTH: 11
<212> TYPE: PRT
<213> ORGANISM: Caenorhabditis elegans
<220> FEATURE:
<223> OTHER INFORMATION: Segment of mec-10 protein

<400> SEQUENCE: 17

Cys Tyr Lys Thr Ser Ser His Gly Ile Pro Met
 1               5                  10

<210> SEQ ID NO 18
<211> LENGTH: 11
<212> TYPE: PRT
<213> ORGANISM: Caenorhabditis elegans
<220> FEATURE:
<223> OTHER INFORMATION: Segment of Deg-1 protein

<400> SEQUENCE: 18

Cys Asp Lys Thr Thr Ala His Gly Ala Lys Arg
 1               5                  10

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      Site-directed mutagenesis primer- forward

<400> SEQUENCE: 19
ccaacacaca cagcccccaaa c                                       21

<210> SEQ ID NO 20
<211> LENGTH: 23
<212> TYPE: DNA
<213> ORGANISM: Artificial Sequence
<220> FEATURE:
```

<223> OTHER INFORMATION: Description of Artificial Sequence:
    Site-directed mutagenesis primer- reverse

<400> SEQUENCE: 20
ccttgacctt ggagtactgg aag                                              23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: A-1
    forward PCR primer

<400> SEQUENCE: 21
acccttgctc tctccaatcc ac                                               22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: A-2
    forward PCR primer

<400> SEQUENCE: 22
ctgcaacaac accaccatcc ac                                               22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: A-3
    forward PCR primer

<400> SEQUENCE: 23
agctccttca ccactctcgt g                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: A-4
    forward PCR primer

<400> SEQUENCE: 24
agctccttca ccactctcgt g                                                21

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: A-5
    forward PCR primer

<400> SEQUENCE: 25
cctctgactc tagtctctgt gtc                                              23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: A-6 forward PCR primer

<400> SEQUENCE: 26
gaccctactc tctcttttcc tg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: A-7
      forward PCR primer

<400> SEQUENCE: 27
gccaactctg ctctctctgc ac                                              22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: A-8
      forward PCR primer

<400> SEQUENCE: 28
cacggaatca ggttgggcct c                                               21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: A-9
      forward PCR primer

<400> SEQUENCE: 29
cctctccacc ctcctccctt c                                               21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: A-10
      forward PCR primer

<400> SEQUENCE: 30
acaggcatct ctctgtaccc ac                                              22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: A-11
      forward PCR primer

<400> SEQUENCE: 31
aacactgagc acctttctcc atc                                             23

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: A-12
      forward PCR primer

```
<400> SEQUENCE: 32
gaccttgatg acaccccat tc                                              22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: A-13
      forward PCR primer

<400> SEQUENCE: 33
tcttcccacc ctctgtccca c                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: A-14
      forward PCR primer

<400> SEQUENCE: 34
agaaccctct gtcccatcgt c                                              21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: A-15
      forward PCR primer

<400> SEQUENCE: 35
gtctgtggtg gagatggctg ag                                             22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: A-16
      forward PCR primer

<400> SEQUENCE: 36
ggtagcctcc accctggcat c                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: A-1
      reverse PCR primer

<400> SEQUENCE: 37
gaactcgatc agggcctcct c                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: A-2
      reverse PCR primer
```

```
<400> SEQUENCE: 38
ggggcagagg gactaaccga c                                            21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: A-3
      reverse primer

<400> SEQUENCE: 39
ggaccctcag gcgctgcaag                                              20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: A-4
      reverse PCR primer

<400> SEQUENCE: 40
gtcaggaaag gagcggagcc catg                                         24

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: A-5
      reverse PCR primer

<400> SEQUENCE: 41
ggagccaggc aggactgact c                                            21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: A-6
      reverse PCR primer

<400> SEQUENCE: 42
cgccatggag caagcaggga g                                            21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: A-7
      reverse PCR primer

<400> SEQUENCE: 43
ccttccaggc ctcccagtca g                                            21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: A-8
      reverse PCR primer

<400> SEQUENCE: 44
```

```
cacggaatca ggttgggcct c                                              21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: A-9
      reverse PCR primer

<400> SEQUENCE: 45
ggggctccct ggagtctcac                                                20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: A-10
      reverse PCR primer

<400> SEQUENCE: 46
tggctcggta acctgtattc tac                                            23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: A-11
      reverse PCR primer

<400> SEQUENCE: 47
acccatccct tccccacact c                                              21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: A-12
      reverse PCR primer

<400> SEQUENCE: 48
cagggaccag ggcaggactg                                                20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: A-13
      reverse PCR primer

<400> SEQUENCE: 49
caggctccat ccaggcacga c                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: A-14
      reverse primer

<400> SEQUENCE: 50
```

```
ctggagacca gtatcggctt c                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: A-15
      reverse PCR primer

<400> SEQUENCE: 51
gcctgggtgg gacaaggaca g                                              21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: A-16
      reverse PCR primer

<400> SEQUENCE: 52
gccttggtgt gagaaacctc tc                                             22

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: B-1
      forward PCR primer

<400> SEQUENCE: 53
atgcctctct gcaggtgcca c                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: B-2
      forward PCR primer

<400> SEQUENCE: 54 ttcccccctaa ccagccctct c                                             21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: B-3
      forward PCR primer

<400> SEQUENCE: 55
tggcctccac agtgtagcct c                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: B-4
      forward PCR primer

<400> SEQUENCE: 56
tggcctccac agtgtagcct c                                              21
```

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: B-5
      forward PCR primer

<400> SEQUENCE: 57
cctgccctgc agctgatgct g                                               21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: B-6
      forward PCR primer

<400> SEQUENCE: 58
cgcagccctc accccaccct c                                               21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: B-7
      forward PCR primer

<400> SEQUENCE: 59
aagcaacccc tctaaacaca g                                               21

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: B-8
      forward PCR primer

<400> SEQUENCE: 60
cctgtgttct ctcattatga ac                                              22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: B-9
      forward PCR primer

<400> SEQUENCE: 61
aacctcttgg ccgcctttct g                                               21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: B-10
      forward PCR primer

<400> SEQUENCE: 62
gcagggacca caacaggcct g                                               21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: B-11
      forward PCR primer

<400> SEQUENCE: 63
gatggcaact tttgcaacca c                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: B-12
      forward PCR primer

<400> SEQUENCE: 64
ggcccatctc gctgcctcct g                                              21

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: B-13
      forward PCR primer

<400> SEQUENCE: 65
caagaatgtg tggcctgag                                                 19

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: B-14
      forward PCR primer

<400> SEQUENCE: 66
caccaacttt ggcttccagc c                                              21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: B-15
      forward PCR primer

<400> SEQUENCE: 67
ctggtggcct tggccaagag                                                20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: B-1
      reverse primer

<400> SEQUENCE: 68
agctgtgcac tccggggcca c                                              21

```
<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence:  B-2
      reverse PCR primer

<400> SEQUENCE: 69
cattgcttga tatgtgccca g                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence:  B-3
      reverse PCR primer

<400> SEQUENCE: 70
catctctact agctcctgct g                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence:   B-4
      reverse PCR primer

<400> SEQUENCE: 71
ccgactgtcc gtaggtgcca g                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence:  B-5
      reverse PCR primer

<400> SEQUENCE: 72
ggttaaagcc tcatggctct g                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence:  B-6
      reverse PCR primer

<400> SEQUENCE: 73
gcccttgggc tccggccata c                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence:  B-7
      reverse PCR primer

<400> SEQUENCE: 74
aggcgtgcac caccttccca c                                              21

<210> SEQ ID NO 75
```

```
<211> LENGTH: 20
<212> TYPE: DNA
<213> ORGANISM: Artificial Sequence
<220> FEATURE:
<223> OTHER INFORMATION: Description of Artificial Sequence: B-8
      reverse PCR primer

<400> SEQUENCE: 75
gatcccccgt gcccccgctc                                              20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: B-9
      reverse PCR primer

<400> SEQUENCE: 76
tgtgcccgcc cacccgcact c                                            21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: B-10
      reverse PCR primer

<400> SEQUENCE: 77 gtggtttgcaa aagttgccat c                                           21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: B-11
      reverse PCR primer

<400> SEQUENCE: 78
ccagccccgc ccaggctcag                                              20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: B-12
      reverse PCR primer

<400> SEQUENCE: 79
agggctgggg tattgggaga c                                            21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: B-13
      reverse PCR primer

<400> SEQUENCE: 80
aaagttggtg tgggcctcca c                                            21

<210> SEQ ID NO 81
<211> LENGTH: 20
```

```
<212> TYPE: DNA
<213> ORGANISM: Artificial Sequence
<220> FEATURE:
<223> OTHER INFORMATION: Description of Artificial Sequence: B-14
      reverse PCR primer

<400> SEQUENCE: 81
ggctgctcag tgagtttcag                                              20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: B-15
      reverse PCR primer

<400> SEQUENCE: 82
gtccagcgtc tgcagacgca g                                            21

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: G-1
      forward PCR primer

<400> SEQUENCE: 83
gtcccatcct cgccatg                                                 17

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: G-2
      forward PCR primer

<400> SEQUENCE: 84
ccctctccct gacttttcct c                                            21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: G-3
      forward PCR primer

<400> SEQUENCE: 85
cgcatctcct cttattcaca g                                            21

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence:  G-4
      forward PCR primer

<400> SEQUENCE: 86
gacccatttt cttcctccat ag                                           22

<210> SEQ ID NO 87
<211> LENGTH: 21
<212> TYPE: DNA
```

```
<213> ORGANISM: Artificial Sequence
<220> FEATURE:
<223> OTHER INFORMATION: Description of Artificial Sequence: G-5
      forward PCR primer

<400> SEQUENCE: 87
caggtggtct tatcctccca g                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: G-6
      forward PCR primer

<400> SEQUENCE: 88
gaggacaggg ctgagtgtgt g                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: G-7
      forward PCR primer

<400> SEQUENCE: 89
tcctgggtct cctctttcag a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: G-8
      forward PCR primer

<400> SEQUENCE: 90
gccctctccc ttgtccctca g                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: G-9
      forward PCR primer

<400> SEQUENCE: 91
cgctttctct ctccgttgta g                                              21

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: G-10
      forward PCR primer

<400> SEQUENCE: 92
ttcacctgtt ggaattttgc ag                                             22

<210> SEQ ID NO 93
<211> LENGTH: 21
<212> TYPE: DNA
<213> ORGANISM: Artificial Sequence
```

-continued

```
<220> FEATURE:
<223> OTHER INFORMATION: Description of Artificial Sequence: G-11
      forward PCR primer

<400> SEQUENCE: 93
ttgatggtgt ggcttggcct g                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: G-12
      forward PCR primer

<400> SEQUENCE: 94
gcagaaagcc aaggagtggt g                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: G-1
      reverse PCR primer

<400> SEQUENCE: 95
ctgcaacatc aacccctaca a                                              21

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: G-2
      reverse PCR primer

<400> SEQUENCE: 96
aatgagaagg tgaaatctta cc                                             22

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: G-3
      reverse PCR primer

<400> SEQUENCE: 97
agagcagcat tctctcctga c                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: G-4
      reverse PCR primer

<400> SEQUENCE: 98
ccttggcaca ggtttcctta c                                              21

<210> SEQ ID NO 99
<211> LENGTH: 21
<212> TYPE: DNA
<213> ORGANISM: Artificial Sequence
<220> FEATURE:
```

<223> OTHER INFORMATION: Description of Artificial Sequence: G-5
      reverse PCR primer

<400> SEQUENCE: 99
ctccaagcct atggaaatga g                                     21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: G-6
      reverse PCR primer

<400> SEQUENCE: 100
cagggctggg tgcccctgcc a                                     21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: G-7
      reverse PCR primer

<400> SEQUENCE: 101
ctggagctgg gtctcactca c                                     21

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: G-8
      reverse PCR primer

<400> SEQUENCE: 102
gttccccact ctgcccaccg                                       20

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: G-9
      reverse PCR primer

<400> SEQUENCE: 103
gaacagggta gaggtaactt ac                                    22

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: G-10
      reverse PCR primer

<400> SEQUENCE: 104
gaaggaagcc actctactca c                                     21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: G-11

```
                              -continued reverse PCR primer

<400> SEQUENCE: 105
tacggggagc ttctggacat g                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence:  G-12
      reverse PCR primer

<400> SEQUENCE: 106
gatctgtctt ctcaaccctg c                                              21
```

METHOD TO DIAGNOSE AND TREAT PATHOLOGICAL CONDITIONS RESULTING FROM DEFICIENT ION TRANSPORT SUCH AS PSEUDOHYPOALDOSTERONISM TYPE-1

This application is a 371 filing of PCT/US98/04681 filed Mar. 11, 1998. This application is related to U.S. Application Ser. No. 60/040,171, filed on Mar. 11, 1997, which is herein incorporated by reference in its entirety.

TECHNICAL FIELD

The invention relates to the fields of detecting and treating homozygous and heterozygous genetic deficiencies in ion transport, particularly alterations in nucleic acid molecules and proteins that give rise to various forms of pseudohypoaldosteronism type-1 (PHA1). More specifically, the invention provides compositions and methods for determining whether an individual is affected by or carriers a mutation a gene that encodes a protein involved in ion transport.

BACKGROUND ART

Background

Pseudohypoaldosteronism type I (PHA1) is a rare salt wasting disease characterized by an often fulminate presentation in the neonatal period with dehydration, hyponatremia, hyperkalaemia, metabolic acidosis, failure to thrive and weight loss despite normal renal glomerular filtration and adrenal function (Cheek, D. et al. *Archives of Dis. in Childhood* 33:252–256 (1958); Dillon, M. J. et al. *Archives of Dis. in Childhood* 55:427–434 (1980); Popow, C., et al. *Acta Paediatr. Scand.* 77:136–141 (1988); Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986). PHA1 is suspected when these infants fail to respond to mineralocorticoids, and the diagnosis is supported by the finding of an elevated plasma aldosterone concentration and plasma renin activity (Dillon, M. J. et al. *Archives of Dis. in Childhood* 55:427–434 (1980); Popow, C., et al. *Acta Paediatr. Scand.* 77:136–141 (1988); Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986). Treatment includes sodium chloride supplementation and treatment with an ion-binding resin or dialysis to reduce life-threatening hyperkalaemia (Cheek, D. et al. *Archives of Dis. in Childhood* 33:252–256 (1958); Dillon, M. J. et al. *Archives of Dis. in Childhood* 55:427–434 (1980); Popow, C., et al. *Acta Paediatr. Scand.* 77:136–141 (1988); Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986; Donnell, G. N., et al. *Am. J. Dis. Child.* 97:813–828 (1959); Mathew, P. M., et al. *Clinical Pediatrics.* 1:58–60 (1993)). Death in the neonatal period is common if the diagnosis is not made.

PHA1 kindreds showing both autosomal recessive and dominant transmission have been described (Hanukoglu, A. *J. Clin. Endocrin. & Metab.* 73,936–944 (1991)). Cases in recessive kindreds typically show mineralocorticoid resistance in the kidney, sweat and salivary glands, and colonic mucosa (Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986; Hanukoglu, A. *J. Clin. Endocrin. & Metab.* 73,936–944 (1991); Hanukoglu, A., et al. *J. Pediatr.* 125: 752–755 (1994); Hogg, R. J., et al. *Pediatric Nephrology* 5:205–210 (1991)); where measured, parents of these cases have had normal aldosterone and renin levels (Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986; Hanukoglu, A. *J. Clin. Endocrin. & Metab.* 73,936–944 (1991)). In contrast, kindreds supporting dominant transmission have also been reported, and in some of these have been shown to have disease limited to the kidney (Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986; Hanukoglu, A. *J. Clin. Endocrin. & Metab.* 73,936–944 (1991); Limal, J. M., et al. Lancet 1:51 (1978); Hanukoglu, A., et al. *Lancet* 1:1359 (1978)). Clinical signs and metabolic abnormalities of some patients improve in the first several years of life, allowing discontinuation of therapy (Cheek, D. et al. *Archives of Dis. in Childhood* 33:252–256 (1958); Dillon, M. J. et al. *Archives of Dis. in Childhood* 55:427–434 (1980); Speiser, P. W., Stoner, E. & New, M. I. Pseudohypoaldosteronism: a review and report of two new cases. In: Mechanisms and clinical aspects of steroid hormone resistance. (eds. Chrousos, G. P., Loriaux, D. T. & Lipsett, M. B.) 173–195. (Plenum Press, New York), 1986; Donnell, G. N., et al. *Am. J. Dis. Child.* 97:813–828 (1959); Hanukoglu, A. *J. Clin. Endocrin. & Metab.* 73,936–944 (1991)); it has been suggested that these patients are most often those with dominant transmission (Hanukoglu, A. *J. Clin. Endocrin. & Metab.* 73,936–944 (1991)).

The pathogenesis of this syndrome has not been elucidated. The triad of renal salt wasting, hyperkalaemia and failure to respond to mineralocorticoids is most compatible with a renal defect in the distal nephron (Cheek, D. et al. *Archives of Dis. in Childhood* 33:252–256 (1958); Rösler, A. *J. Clin. Endocrin. & Metab.* 59:689–700 (1984)). While mineralocorticoid receptor levels in affected patients have been found to be low (Armanini, D. et al. *N. Eng. J Med.* 313:1178–1181 (1985); Kuhnle U. et al. *J. Clin. Endocrin. & Metab.* 70:638–641 (1990); Bosson, D. et al. Acta Endo. 113:S376–S381 (1986)) molecular studies have revealed no evidence for a primary defect in the mineralocorticoid receptor (Komesaroff, P. A., et al. *J. Clin. Endocrin. & Metab.* 79:27–31 (1994); Zennaro, M. C., et al. *J. Clin. Endocrin. & Metab.* 79:32–38 (1994)).

Electrogenic transepithelial sodium transport is the rate limiting step in sodium reabsorption in the distal nephron, the distal colon, salivary and sweat glands, and lung epithelia (Horisberger, J. D., et al. *Cell Physiol. Biochem.* 32:283–294 (1993)). In the kidney, this electrogenic sodium transport is positively regulated by aldosterone (Rossier, B. C. & Palmer, L. G. Mechanism of aldosterone action on sodium and potassium transport. In: The Kidney, physiology and pathophysiology (eds. Seldin, D. W. and Giebisch, G.) 1373–1409 (Raven Press, New York, 1992)) and is mediated by the amiloride-sensitive epithelial sodium channel (ENaC). This channel composed of at least three subunits of similar structure (Canessa, C. M., et al. *Nature* 361:467–470

(1993); Canessa, C. M. et al. *Nature* 367:463–467 (1994)), each with intracellular amino and carboxy termini, two transmembrane spanning domains, and a large extracellular loop. In humans, αENaC is present on human chromosome 12, while b and g are tightly linked on chromosome 1622.

Mutations resulting in constitutive activation of ENaC activity have been shown to cause an autosomal dominant form of hypertension, Liddle's syndrome (Shimkets, R. A. et al. *Cell* 79:407–414 (1994); Hansson, J. H. et al. *Nature Genetics* 11:76–82 (1995); Hansson, J. H. et al. *Proc. Nat. Acad. Sci. USA* 92:11495–11499 (1995); Schild, L. et al. *Proc. Natn. Acad. Sci. USA* 92:5699–5703 (1995)), which is characterized by volume expansion, hypokalaemia and alkalosis.

The present invention provides compositions and methods that can be used to differentiate and diagnose ion transport deficiencies, particularly PHA1. The present invention further provides methods and compositions that can be used to identify heterozygous carriers for this disorder. Carriers, though not displaying severe clinical symptoms, nonetheless display mild to moderate pathologies.

SUMMARY OF THE INVENTION

The present invention is based, in part, on the identification of the role of the epithelial sodium channel (ENaC) in pathological condition associated with abnormal ion transport, particularly PHA1, hypokalaemic alkalosis, hypokalaemic acidosis and salt wasting. The present invention specifically provides the amino acid sequences of several human wild-type and altered variants of the ENaC proteins as well as the nucleotide sequence that encodes these variants. These proteins and nucleic acid molecules can be used in diagnosing ion transport disorders and in developing methods and agents for treating these pathologies.

BRIEF DESCRIPTIONS OF THE DRAWINGS

FIG. 1. PHA1 Kindreds

The family relationships of 5 PHA1 kindreds in which mutations have been identified are shown. All affected subjects are the product of consanguineous union. Subjects classified as affected are indicated by filled symbols; unaffected subjects are indicated by unfilled symbols; deceased subjects are indicated by a diagonal line; index cases are indicated by an arrow; living subjects who were not sampled are indicated by dots. Within each kindred, each sampled individual is identified by a unique number, which is shown above and to the left of their respective symbol. Below each symbol, the SSCP genotype at either αENaC (PHA K10, K13, K14 and K3) or βENaC (PHA K8) is shown. The symbol + denotes the normal SSCP variant, and the numbers 1, 2, and 3 indicate the αENaC codon 68 frameshift, αENaC codon 508 stop, and βENaC G37S mutations, respectively.

FIG. 2. Mutations in ENaC Subunits in PHA1 Patients

In each panel, variants identified by SSCP in PHA1 kindreds are shown. Individuals are numbered as in FIG. 1, and representative autoradiograms are shown. SSCP genotypes, as well as marker genotypes, were confirmed from at least two independent amplifications for each individual. Affected individuals are indicated by an asterisk, and the novel SSCP variants that are homozygous in affected subjects are indicated by arrows; these variants are numbered as in FIG. 1. At the bottom of each panel, the DNA sequence of the mutant allele (left) and corresponding wild-type allele (right) is shown; deleted bases are indicated by a bracket in panel A, and single base substitutions are indicated by asterisks in panels B and C SEQ ID NO: 1 (CCACCATCCACGG); SEQ ID NO: 2 (CCACCACACGG); SEQ ID NO: 3 (CTGTCGCGA); SEQ ID NO: 4 (CTGTCACGA); SEQ ID NO: 5 (CACGGCCCC); and SEQ ID NO: 6 (CACAGCCCC).

2a. Affected subjects in PHA kindreds K10, K13 and K14 are homozygous for the same 2 base pair deletion introducing a frameshift at codon 68 of αENaC, and this variant cosegregates with the disease. The DNA sequence extending from the last two bases of codon 66 to the first two bases of codon 70 of the wild type sequence are shown in the sense orientation. The last two bases of codon I68 are absent in the mutant.

2b. Homozygous variant in αENaC introducing a premature termination codon at codon 508 of PHA K3. DNA sequence encoding amino acids 507–509 are shown in the antisense orientation; in the sense orientation, CGA encoding R508 is mutated to TGA, encoding stop 508.

2c. Homozygous variant in βENaC encoding G37S in affected subjects of PHA K8. DNA sequence of codons 36–38 are shown in the sense orientation. The sequence GGC encoding G37 is mutated to AGC encoding S37.

FIG. 3. Consequences of Mutations Identified in PHA1 Kindreds

3a. The effects of mutations in α and βENaC in PHA1 kindreds are shown. ENaC subunits are drawn as spanning the plasma membrane twice (Canessa C. M., et al. *Am. J. Ped.* 267:C1682–169 (1994)), and amino and carboxyl termini are indicated. Arrows indicate the position of identified mutations in each subunit. The kindreds in which each mutation is found are indicated. Mutation in αENaC introduces a frameshift mutation at codon 68 proximal to the first transmembrane domain; this mutation is found in 3 kindreds. A mutation in PHA K3 introduces a premature termination codon into the extracellular domain of αENaC, and a mutation in βENaC in PHA K8 introduces a missense mutation, changing glycine at residue 37 to serine.

3b. G37S mutation in βENaC occurs in a conserved ENaC segment. Amino acid sequences preceding the first transmembrane domain of different members of the ENaC family are shown. The prefix h, r, and x denote genes from human, rat and Xenopus laevis, respectively (Canessa, C. M., et al. *Nature* 361:467–470 (1993); Canessa, C. M. et al. *Nature* 367:463–467 (1994); McDonald, F. J., et al. *Am. J Physiol.* 268:L728–734 (1994); McDonald, F. J., et al. *Am. J Physiol.* 268: C1157–C1163 (1995); Puoti, A. et al. *Am J Physiol.* 269:C188–C197 (1995); Waldmann, R., et al. *J. of Biol. Chem.* 270:27411–27414 (1995)); mec-10 and Deg-1 are from C. elegans (Huang, M. et al. *Nature* 367:467–470 (1994); Chalfie, M. et al. *Nature* 345:410–416 (1990)). Those residues that are identical in a, b and g subunits from all species are shaded. The completely conserved glycine at position 37 of hbENAC is mutated to serine in PHA kindred 8. SEQ ID NO: 7 (hβENaC); SEQ ID NO: 8 (rβENaC); SEQ ID NO: 9 (xβENaC); SEQ ID NO: 10 (hαENaC); SEQ ID NO: 11 (rαENaC); SEQ ID NO: 12 (xαENaC); SEQ ID NO: 13 (hγENaC); SEQ ID NO: 14 (rγENaC); SEQ ID NO: 15 (xγENaC); SEQ ID NO: 16 (hδENaC); SEQ ID NO: 17 (mec-10); and SEQ ID NO: 18 (Deg-1).

Figure 4:
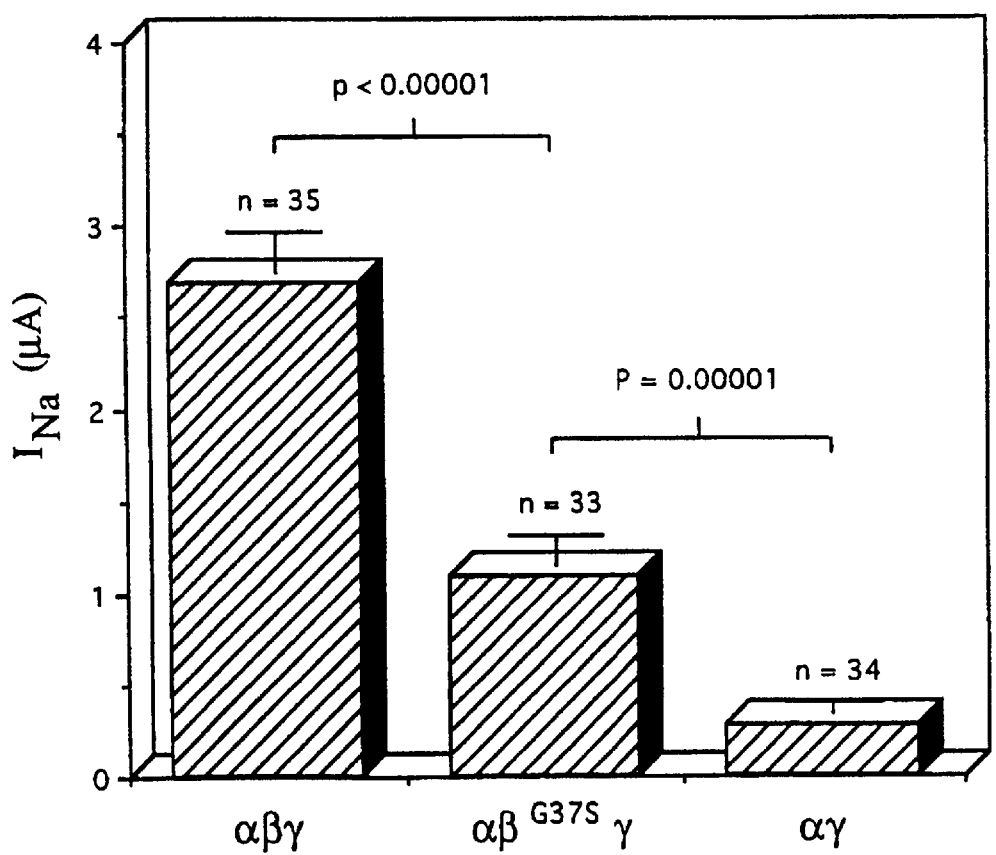

FIG. 4. Effect of βENaC G37S on Amiloride-sensitive Na$^+$Channel Activity in Xenopus Oocytes cRNAs encoding normal or mutant ENaC subunits were coinjected into Xenopus oocytes, and the resulting amiloride-sensitive sodium current was measured. βENaC containing the G37S mutation was coexpressed with α and γ subunits (represented as αβ37Sγ). Oocytes injected either with normal α, β and γ or only α and γ subunits (αβγ and αγ, respectively) served as controls. The mean of the absolute values of the amiloride-sensitive sodium current obtained from 33 to 35 oocytes from 5 different batches of oocytes is shown. Error bars represent the SEM. The p values for t-tests comparing activity of mutant and wild-type channels are indicated.

MODES OF CARRYING OUT THE INVENTION

I. General Description

The present invention is based, in part, on the identification of the role of the epithelial sodium channel (ENaC) in pathological conditions associated with abnormal ion transport, particularly PHA1, hypokalaemic acidosis and salt wasting. The present invention specifically provides the amino acid sequences of several human wild-type and altered variants of the α, β and γ subunits of the ENaC protein, as well as the nucleotide sequence that encodes these variants. These proteins and nucleic acid molecules can be used in diagnosing ion transport disorders and in developing methods and agents for treating these pathologies.

II. Specific Embodiments

A. ENaC Protein

Prior to the present invention the art had identified: the amino acid sequence of the three subunits of human ENaC. However, prior to the present invention, (1) no one had identified that alterations in human variants of the ENaC protein that produce inactive ENaC result in viable individuals that suffer from pathologies caused by abnormal ion transport; (2) no one had characterized naturally occurring human wild-type variants of the subunits of ENaC; (3) no one had characterized human altered variants of the ENaC protein that yielded inactive ENaC; and (4) no one had shown that pathological conditions that are a result of abnormal ion transport, such as PHA1, could be identified by analyzing a sample for the presence of a wild-type or an altered variant of the ENaC protein. The present invention provides, in part, the amino acid sequences of wild-type human ENaC protein and altered variants of the human ENaC protein that give rise to ion transport deficiencies, as well as the nucleotide sequence of the encoding nucleic acid molecules.

In one embodiment, the present invention provides the ability to produce previously unknown altered variants of the human ENaC proteins using the cloned nucleic acid molecules herein described.

As used herein, a wild-type human ENaC protein refers to a protein that has the amino acid sequence of a wild-type allelic variant of human ENaC. The ENaC protein is comprised of 3 subunits: the α, β and γ subunits, referred to herein as αENaC, βENaC and γENaC, respectively. For the sake of convenience, the collective subunits will be referred to as the ENaC protein. The wild-type ENaC proteins of the present invention include the specifically identified and characterized variant herein described as well as allelic variants that can be isolated and characterized without undue experimentation following the methods outlined below. For the sake of convenience, all of the wild-type human ENaC proteins of the present invention will be collectively referred to as the wild-type ENaC proteins or the wild-type human ENaC proteins of the present invention.

The term "wild-type human ENaC proteins" includes all naturally occurring allelic variants of the human ENaC protein that posses normal ENaC activity. Allelic variants, though possessing a slightly different amino acid sequence than those recited above, will posses the ability to be a sodium transporter. Typically, allelic variants of the wild-type ENaC protein will contain conservative amino acid substitutions from the wild-type sequences herein described or will contain a substitution of an amino acid from a corresponding position in an ENaC homologue (an ENaC protein isolated from an organism other than human).

As used herein, a mutated or altered human ENaC protein refers to a protein that has the amino acid sequence of a mutated or altered allelic variant of human ENaC that produces an ENaC protein with reduced ion transport capability. FIG. 3 provides the amino acid sequences of several mutated or altered allelic variants of each of the three subunits of human ENaC protein. The mutated or altered ENaC proteins of the present invention include those specifically identified and characterized herein as well as allelic variants that can be isolated and characterized without undue experimentation following the methods outlined below. For the sake of convenience, all of the mutated or altered human ENaC proteins of the present invention will be collectively referred to as mutated or altered human ENaC proteins or the mutated or altered human ENaC proteins of the present invention.

The term "mutated or altered human ENaC proteins" includes all naturally occurring allelic variants of the human ENaC protein that do not posses normal ENaC activity. Mutated or altered allelic variants will be not be able to transport sodium or will transport sodium at a reduced rate when compared to wild-type ENaC. Typically, mutated or altered ENaC protein will contain: non-conservative amino acid substitutions from the wild-type sequences herein described; a substitution of an amino acid other than the amino acid found in a corresponding position in an ENaC homologue (an ENaC protein isolated from an organism other than human); a frame shift mutation, an insertion of a stop codon; or a deletion or insertion of one or more amino acids into the ENaC sequence.

The ENaC proteins of the present invention (wild-type and mutated variants) are preferably in isolated from. As used herein, a protein is said to be isolated when physical, mechanical or chemical methods are employed to remove the ENaC protein from cellular constituents that are normally associated with the protein. A skilled artisan can readily employ standard purification methods to obtain an isolated ENaC protein. The nature and degree of isolation will depend on the intended use.

The cloning of ENaC encoding nucleic acid molecules makes it possible to generate defined fragments of the ENaC proteins of the present invention. As discussed below, fragments of the ENaC proteins of the present invention are particularly useful in generating domain specific antibodies, in identifying agents that bind to an ENaC protein and in identifying ENaC intra- or extracellular binding partners.

Fragments of the ENaC proteins can be generated using standard peptide synthesis technology and the amino acid sequences disclosed herein. Alternatively, recombinant methods can be used to generate nucleic acid molecules that encode a fragment of the ENaC protein. by FIG. 3 identifies amino acid residues that are altered from wild-type residues in altered variants of the ENaC proteins described herein. Fragments containing these residues/alterations are particularly useful in generating altered variant specific anti-ENaC antibodies.

As described below, members of the ENaC family of proteins can be used for, but are not limited to: 1) a target to identify agents that block or stimulate ENaC activity, 2) a target or bait to identify and isolate binding partners that bind an ENaC protein, 3) identifying agents that block or stimulate the activity of an ENaC protein and 4) an assay target to identify ENaC mediated activity or disease.

B. Anti-ENaC Antibodies

The present invention further provides antibodies that selectively bind one or more of the ENaC proteins of the present invention. The most preferred antibodies will bind to an altered variant of an ENaC protein but not to a wild-type variant or will bind to a wild-type variant of an ENaC protein but not to an altered variant. Anti-ENaC antibodies that are particularly contemplated include monoclonal and polyclonal antibodies as well as fragments containing the antigen binding domain and/or one or more complement determining regions.

Antibodies are generally prepared by immunizing a suitable mammalian host using an ENaC protein, or fragment, in isolated or immunoconjugated variant (Harlow Antibodies, Cold Spring Harbor Press, NY (1989)). FIG. 3 identifies several regions of the ENaC protein that have been shown to be mutated in various altered variants of the ENaC protein described herein. Fragments containing these residues are particularly suited in generating wild-type or mutated-variant specific anti-ENaC antibodies.

Methods for preparing a protein for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective.

Administration of the ENaC immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the ENaC protein or peptide fragment. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of the transporter can also be produced in the context of chimeric or CDR grafted antibodies of multiple species origin.

As described below, anti-ENaC antibodies are useful as modulators of ENaC activity, are useful in immunoassays for detecting ENaC expression/activity and for purifying wild-type and altered variants of the ENaC proteins.

C. ENaC Encoding Nucleic Acid Molecules

As described above, the present invention is based, in part, on isolating nucleic acid molecules from humans that encode wild-type or altered variants of the ENaC proteins. Accordingly, the present invention further provides nucleic acid molecules that encode the herein disclosed wild-type and altered variants of the ENaC protein, as herein defined, preferably in isolated form. For convenience, all ENaC encoding nucleic acid molecules will be referred to as ENaC encoding nucleic acid molecules, the ENaC genes, or ENaC. The nucleotide sequence of identified wild-type and altered ENaC encoding nucleic acid molecules are provided in FIG. 2.

As used herein, a "nucleic acid molecule" is defined as an RNA or DNA molecule that encodes a peptide as defined above, or is complementary to a nucleic acid sequence encoding such peptides. Particularly preferred nucleic acid molecules will have a nucleotide sequence identical to or complementary to the human cDNA sequences herein disclosed. Specifically contemplated are genomic DNA, cDNA, mRNA and antisense molecules, as well as nucleic acids based on an alternative backbone or including alternative bases, whether derived from natural sources or synthesized. Such nucleic acid molecules, however, are defined further as being novel and unobvious over any prior art nucleic acid molecules encoding non-human homologues of ENaC isolated from non-human organisms and known human ENaC proteins.

As used herein, a nucleic acid molecule is said to be "isolated" when the nucleic acid molecule is substantially separated from contaminant nucleic acid molecules that encode polypeptides other than ENaC. A skilled artisan can readily employ nucleic acid isolation procedures to obtain an isolated ENaC encoding nucleic acid molecule.

The present invention further provides fragments of the ENaC encoding nucleic acid molecules of the present invention. As used herein, a fragment of an ENaC encoding nucleic acid molecule refers to a small portion of the entire protein encoding sequence. The size of the fragment will be determined by its intended use. For example, if the fragment is chosen so as to encode an active portion of the ENaC protein, such an intracellular or extracellular domain, then the fragment will need to be large enough to encode the functional region(s) of the ENaC protein. If the fragment is to be used as a nucleic acid probe or PCR primer, then the fragment length is chosen so as to obtain a relatively small number of false positives during probing/priming. Table 2 identifies fragments of the ENaC genes that are particularly useful as selective hybridization probes or PCR primers. Such fragments contain regions that are conserved among wild-type or altered variants of ENaC, regions of homology that are shared with the previously identified ENaC genes, and regions that are altered in altered variants of the ENaC genes.

Fragments of the ENaC encoding nucleic acid molecules of the present invention (i.e., synthetic oligonucleotides) that are used as probes or specific primers for the polymerase chain reaction (PCR), or to synthesize gene sequences encoding ENaC proteins, can easily be synthesized by chemical techniques, for example, the phosphotriester method of Matteucci, et al., *J Am Chem Soc* (1981) 103:3185–3191 or using automated synthesis methods. In addition, larger DNA segments can readily be prepared by well known methods, such as synthesis of a group of oligonucleotides that define various modular segments of the ENaC gene, followed by ligation of oligonucleotides to build the complete modified ENaC gene.

The ENaC encoding nucleic acid molecules of the present invention may further be modified so as to contain a detectable label for diagnostic and probe purposes. As described above, such probes can be used to identify nucleic acid molecules encoding other allelic variants of wild-type or altered ENaC proteins and as described below, such probes can be used to diagnosis the presence of an altered variant of an ENaC protein as a means for diagnosing a pathological condition caused by abnormal ion transport. A variety of such labels are known in the art and can readily be employed with the ENaC encoding molecules herein described. Suitable labels include, but are not limited to, biotin, radiolabeled nucleotides, biotin, and the like. A skilled artisan can employ any of the art known labels to obtain a labeled ENaC encoding nucleic acid molecule.

D. Isolation of Other Wild-Type and Altered Forms of ENaC Encoding Nucleic Acid Molecules As described above, the identification of the role of the ENaC proteins in the pathology/severity of ion transport mediated deficiencies, particularly PHA1, has made possible the identification of several altered variants of the ENaC proteins that confer a pathology associated with abnormal (decreased) ion transport. These observations allow a skilled artisan to isolate nucleic acid molecules that encode other wild-type and altered variants of the ENaC proteins, in addition to the sequence herein described.

Essentially, a skilled artisan can readily use the amino acid sequence of the human ENaC protein to generate antibody probes to screen expression libraries prepared from cells. Typically, polyclonal antiserum from mammals such as rabbits immunized with the purified protein (as described below) or monoclonal antibodies can be used to probe a human cDNA or genomic expression library, such as lambda gtll library, prepared from a normal or effected individual, to obtain the appropriate coding sequence for wild-type or altered variants of the ENaC protein. The cloned cDNA sequence can be expressed as a fusion protein, expressed directly using its own control sequences, or expressed by constructions using control sequences appropriate to the particular host used for expression of the enzyme. FIG. 3 identifies important operative domains and domains that have been shown to contain alterations in mutated variants of the ENaC protein. Such regions are preferred sources of antigenic portions of the ENaC protein for the production of probe, diagnostic, and therapeutic antibodies.

Alternatively, a portion of the ENaC encoding sequence herein described can be synthesized and used as a probe to retrieve DNA encoding a member of the ENaC family of proteins from individuals that have normal ion transport or from individuals suffering from a pathological condition that is a result of abnormal ion transport. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives. This method can be used to identify and isolate altered and wild-type variants of the ENaC encoding sequences.

Additionally, pairs of oligonucleotide primers can be prepared for use in a polymerase chain reaction (PCR) to selectively amplify/clone an ENaC-encoding nucleic acid molecule, or fragment thereof. A PCR denature/anneal/extend cycle for using such PCR primers is well known in the art and can readily be adapted for use in isolating other ENaC encoding nucleic acid molecules. Table 2 identifies regions of the human ENaC gene that are particularly well suited for use as a probe or as primers. In general; the preferred primers will flank one or more exons of the ENaC encoding nucleic acid molecule.

E. Methods for Identifying Pathological Conditions Involving Abnormal Ion Transport The present invention further provides methods for identifying cells and individuals expressing active and altered variants of the ENaC protein or the ENaC gene. Such methods can be used to diagnose biological and pathological processes associated with altered (decreased) ion transport, particularly PHA1, the progression of PHA1, the susceptibility of PHA1 to treatment and the effectiveness of treatment for PHA1. The methods of the present invention are particularly useful in identifying carriers of ion transport deficiencies, particularly PHA1s, as well as in differentiating between PHA1 and other ion transport disorders. Specifically, the presence of wild-type or altered variants of an ENaC protein can be identified by determining whether a wild-type or altered variant of the ENaC protein, or nucleic acid encoding the ENaC protein, is expressed in a cell. The expression of an altered variant, or departure from the normal level of ENaC expression, (decrease in expression) can be used as a means for diagnosing pathological conditions mediated by abnormal ENaC activity/expression, differentiating between various ion transport deficiencies, and for identifying carriers of an ion transport deficiency.

A variety of immunological and molecular genetic techniques can be used to determine if a wild-type or an altered variant of an ENaC protein is expressed/produced in a particular cell and/or the level at which the protein is expressed. The preferred methods will identify whether a wild-type or mutated from of the ENaC protein is expressed.

In general, an extract containing nucleic acid molecules or an extract containing proteins is prepared from cells of an individual. The extract is then assayed to determine whether an ENaC protein, or an ENaC encoding nucleic acid molecule, is produced in the cell. The type of protein/nucleic acid molecule expressed and/or the degree/level of expression, provides a measurement of the nature and degree of ENaC activity.

For example, to perform a diagnostic test based on nucleic acid molecules, a suitable nucleic acid sample is obtained and prepared from a subject using conventional techniques. DNA can be prepared, for example, simply by boiling a sample in SDS. Most typically, for nucleic acid samples, a blood sample, a buccal swab, a hair follicle preparation or a nasal aspirate is used as a source of cells to provide the nucleic acid molecules. The extracted nucleic acid can then be subjected to amplification, for example by using the polymerase chain reaction (PCR) according to standard procedures, to selectively amplify an ENaC encoding nucleic acid molecule or fragment thereof. The size of the amplified fragment (typically following restriction endonuclease digestion) is then determined using gel electrophoresis or the nucleotide sequence of the fragment is determined (for example, see Weber and May *Am J Hum Genet* (1 989) 44:388–339; Davies, J. et al. *Nature* (1994) 371:130–136)). The resulting size of the fragment or sequence is then compared to the known wild-type, predicted wild-type, known altered variants and predicted altered variants of the ENaC protein. Using this method, the presence of wild-type or altered variants of an ENaC protein can be differentiated and identified.

Alternatively, the presence or absence of one or more single base-pair polymorphism(s) within an ENaC encoding nucleic acid molecule can be determined by conventional methods which included, but are not limited to, manual and automated fluorescent DNA sequencing, selective hybridization probes, primer extension methods (Nikiforov, T. T. et al. *Nucl Acids Res* (1994) 22:4167–4175); oligonucleotide ligation assay (OLA) (Nickerson, D. A. et al. *Proc Natl Acad Sci USA* (1990) 87:8923–8927); allele-specific PCR methods (Rust, S. et al. *Nucl Acids Res* (1993) 6:3623–3629); RNase mismatch cleavage, single strand conformation polymorphism (SSCP) (Orita, M. et al., *Proc Natl Acad Sci USA* 86:2766–2770 (1989)), denaturing gradient gel electrophoresis (DGGE) and the like. The present diagnosis method is particularly well suit for use in biochip technologies that are being developed to be used to identify whether one of many sequence variations is present in a sample. A skilled artisan can readily adapt any nucleic acid analytical method for use in determining whether a sample contains nucleic acid molecules that encode a wild-type or altered variant of an ENaC protein.

To perform a diagnostic test based on proteins, a suitable protein sample is obtained and prepared from a subject using conventional techniques. Protein samples can be prepared, for example, simply by mixing the sample with SDS followed by salt precipitation of a protein fraction. Typically, for protein samples, a blood sample, a buccal swab, a nasal aspirate, or a biopsy of cells from tissues expressing an ENaC protein is used as a source of cells to provide the protein molecules. The extracted protein can then be analyzed to determine the presence of a wild-type or altered variant of an ENaC protein using known methods. For example, the presence of specific sized or charged variants of a protein can be identified using mobility in an electric filed. Alternatively, wild-type or altered variant specific antibodies can be used. A skilled artisan can readily adapt known protein analytical methods to determine if a sample contains a wild-type and/or altered variant of an ENaC protein.

EnaC expression can also be used in methods to identify disorders that occur as a result of a decrease in the expression of a naturally occurring ENaC gene. Specifically, nucleic acid probes that detect. mRNA can be used to detect cells or tissues that express an ENaC protein and the level of such expression.

The presence of only an altered variant of an ENaC protein (homozygous state) in a sample is diagnostic of PHA1. Altered variants of the ENaC protein, when present in sample that additionally contains a wild-type variant of ENaC (heterozygous state), is diagnostic for carriers of PHA1 and individuals expressing lower levels of active ENaC. Decreased ENaC activity leads to minor ion transport deficiencies and a susceptibility to adverse drug reaction.

Alternatively, ENaC expression can also be used in methods to identify agents that increase or decrease the level of expression of a naturally occurring ENaC gene. For example, cells or tissues expressing an ENaC protein can be contacted with a test agent to determine the effects of the agent on ENaC expression. Agents that activate ENaC expression can be used as an agonist of ENaC activity whereas agents that decrease ENaC expression can be used as an antagonist of ENaC activity.

F. rDNA Molecules Containing an ENaC Encoding Nucleic Acid Molecule

The present invention further provides recombinant DNA molecules (rDNAs) that contain one or more of the wild-type or altered ENaC encoding sequences herein described, or a fragment of the herein-described nucleic acid molecules. As used herein, an rDNA molecule is a DNA molecule that has been subjected to molecular manipulation in vitro. Methods for generating rDNA molecules are well known in the art, for example, see Sambrook et al., *Molecular Cloning* (1989). In the preferred rDNA molecules, an ENaC encoding DNA sequence that encodes a wild-type or altered variant of the ENaC protein is operably linked to one or more expression control sequences and/or vector sequences. Most preferably, the ENaC encoding nucleic acid molecules will encode one of the novel altered variants herein described.

The choice of vector and/or expression control sequences to which one of the ENaC encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of an ENaC encoding sequence included in the rDNA molecule.

Expression control elements that are used for regulating the expression of an operably linked protein encoding sequence are known in the art and include, but are not limited to, inducible promoters, constitutive promoters, secretion signals, enhancers, transcription terminators and other regulatory elements. Preferably, an inducible promoter that is readily controlled, such as being responsive to a nutrient in the host cell's medium, is used.

In one embodiment, the vector containing an ENaC encoding nucleic acid molecule will include a prokaryotic replicon, i.e., a DNA sequence having the ability to direct autonomous replication and maintenance of the recombinant DNA molecule intrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and translation) of the ENaC encoding sequence in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories (Richmond, Calif.), pPL and pKK223 available from Pharmacia, Piscataway, N.J.

Expression vectors compatible with eukaryotic cells, preferably those compatible with vertebrate cells, can also be used to variant rDNA molecules that contain an ENaC encoding sequence. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. Southern et al., *J Mol Anal Genet*

(1982)1:327–341. Alternatively, the selectable marker can be present on a separate plasmid, and the two vectors are introduced by cotransfection of the host cell, and selected by culturing in the presence of the appropriate drug for the selectable marker.

G. Host Cells Containing an Exogenously Supplied ENaC Encoding Nucleic Acid Molecule The present invention further provides host cells transformed with a nucleic acid molecule that encodes one of the human wild-type or altered ENaC protein of the present invention. The host cell can be either prokaryotic or eukaryotic. Eukaryotic cells useful for expression of an ENaC protein are not limited, so long as the cell line is compatible with cell culture methods and compatible with the propagation of the expression vector and expression of an ENaC gene. Preferred eukaryotic host cells include, but are not limited to, yeast, insect and mammalian cells, preferably vertebrate cells such as those from a mouse, rat, monkey or human fibroblastic cell line, the most preferred being cells that do not naturally express a human ENaC protein.

Any prokaryotic host can be used to express an ENaC-encoding rDNA molecule. The preferred prokaryotic host is *E. coli*.

Transformation of appropriate cell hosts with an rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc Acad Sci USA* (1972) 69:2110; and Maniatis et al., *Molecular Cloning, A Laboratory Manual*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373–76.

Successfully transformed cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method.

H. Production of an ENaC Protein Using an rDNA Molecule

The present invention further provides methods for producing a human wild-type or altered ENaC protein that uses one of the ENaC encoding nucleic acid molecules herein described. In general terms, the production of a recombinant human wild-type or altered ENaC protein typically involves the following steps.

First, a nucleic acid molecule is obtained that encodes an ENaC protein, such as the nucleic acid molecule depicted in FIG. 2. If the ENaC encoding sequence uninterrupted by introns, it is directly suitable for expression I any host. If not, then a spliced variant of the ENaC encoding nucleic acid molecule can be generated and used or the intron containing nucleic acid molecule can be used in a compatible eukaryotic expression system.

The ENaC encoding nucleic acid molecule is then preferably placed in an operable linkage with suitable control sequences, as described above, to variant an expression unit containing the ENaC encoding sequence. The expression unit is used to transform a suitable host and the transformed host is cultured under conditions that allow the production of the ENaC protein. Optionally the ENaC protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in an appropriate host. The construction of expression vectors that are operable in a variety of hosts is accomplished using an appropriate combination of replicons and control sequences. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with ENaC encoding sequences to produce an ENaC protein. Particularly well suited are expression systems that result in the production of lipid vesicles containing the expressed protein. Such lipid containing vesicles are well suited for identifying agonists and antagonists of the ENaC protein.

I. Ion Transport

As provided above, alterations in the ENaC protein cause pathological conditions that are a result of abnormal ion transport. Accordingly, the wild-type and altered variants of the ENaC proteins of the present invention can be used in methods to alter the extra or intracellular concentration of sodium. In general, the extra or intracellular concentration of sodium can be altered by altering the expression of an ENaC protein or the activity of an ENaC protein.

There are a number of situation in which it is desirable to alter the extra or intracellular concentration of sodium. Abnormal extra or intracellular sodium leads to salt wasting and hypokalaemic acidosis. Hence, an ENaC protein, or ENaC gene, can be used as a target for, or as means to alter extra or intracellular sodium concentration. For example, an ENaC gene can be introduced and expressed in cells to increase ENaC expression. This provides a means and methods for altering extra and intracellular ion levels.

There are pathological conditions characterized by inappropriate extra or intracellular sodium concentrations. For example, PHA1, hypokalaemic acidosis and salt wasting are all associated with abnormal intracellular or extracellular sodium concentration. Accordingly, ENaC activity/expression is targeted as a means of treating these conditions. Various methods for regulating ENaC activity/expression are discussed in detail below.

J. Identification of Agents that Bind to an ENaC Protein

Another embodiment of the present invention provides methods for identifying agents that are agonists or antagonists of the ENaC proteins herein described. Specifically, agonists and antagonists of an ENaC protein can be first identified by the ability of the agent to bind to one of the wild-type or altered variants of the ENaC protein herein described. Agents that bind to an ENaC protein can then be tested for the ability to stimulate or block sodium transport in an ENaC expressing cell.

In detail, an ENaC protein is mixed with an agent. After mixing under conditions that allow association of ENaC with the agent, the mixture is analyzed to determine if the agent bound the ENaC protein. Agonists and antagonists are identified as being able to bind to an ENaC protein, The ENaC protein used in the above assay can be: an isolated and fully characterized protein, a partially purified protein, a cell that has been altered to express an ENaC protein or a fraction of a cell that has been altered to express an ENaC protein. Further, the ENaC protein can be the entire ENaC protein, a specific fragment of the ENaC protein or a single subunit of the ENaC protein. It will be apparent to one of ordinary skill in the art that so long as the ENaC protein can be assayed for agent binding, e.g., by a shift in molecular weight or change in cellular ion content, the present assay can be used.

The method used to identify whether an agent binds to an ENaC protein will be based primarily on the nature of the ENaC protein used. For example, a gel retardation assay can be used to determine whether an agent binds to a soluble fragment of an ENaC protein whereas patch clamping, voltage clamping, ion-sensitive microprobes or ion-sensitive chromaphores can be used to determine whether an agent binds to a cell expressing an ENaC protein and affects the activity of the expressed protein. A skilled artisan can readily employ numerous techniques for determining whether a particular agent binds to an ENaC protein.

Once binding is demonstrated, the agent can be further tested for the ability to modulate the activity of a wild-type or altered variant of the ENaC protein using a cell or oocyte expression system and an assay that detects ENaC activity. For example, voltage or patch clamping, ion-sensitive microprobes or ion-sensitive chromaphores and expression in Xenopus oocytes or recombinant host cells can be used to determine whether an agent that binds an ENaC protein can agonize or antagonize ENaC activity.

As used herein, an agent is said to antagonize ENaC activity when the agent reduces ENaC activity. The preferred antagonist will selectively antagonize ENaC, not affecting any other cellular proteins, particularly other ion transport proteins. Further, the preferred antagonist will reduce ENaC activity by more than 50%, more preferably by more than 90%, most preferably eliminating all ENaC activity.

As used herein, an agent is said to agonize ENaC activity when the agent increases ENaC activity. The preferred agonist will selectively agonize altered variants of ENaC, not affecting any other cellular proteins, particularly other ion transport proteins. Further, the preferred agonist will increase ENaC activity by more than 50%, more preferably by more than 90%, most preferably more than doubling the level of ENaC activity.

Agents that are assayed in the above method can be randomly selected or rationally selected or designed. As used herein, an agent is said to be randomly selected when the agent is chosen randomly without considering the specific sequences of the ENaC protein. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Agents can be rationally selected or rationally designed by utilizing the peptide sequences that make up the ENaC protein. For example, a rationally selected peptide agent can be a peptide whose amino acid sequence is identical to a fragment of an ENaC protein.

The agents of the present invention can be, as examples, peptides, small molecules, and vitamin derivatives, as well as carbohydrates. A skilled artisan can readily recognize that there is no limit as to the structural nature of the agents of the present invention. One class of agents of the present invention are peptide agents whose amino acid sequences are chosen based on the amino acid sequence of the ENaC protein.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the ENaC protein. As described above, antibodies are obtained by immunization of suitable mammalian subjects with peptides, containing as antigenic regions, those portions of the ENaC protein intended to be targeted by the antibodies Critical regions include the domains identified in FIG. 3.

K. Uses of Agents that Bind to an ENaC Protein

As provided in the Background section, the ENaC proteins are involved in regulating intracellular and extracellular sodium concentration. Agents that bind an ENaC protein and act as an agonist or antagonist can be used to modulate biological and pathologic processes associated with ENaC function and activity. In detail, a biological or pathological process mediated by ENaC can be modulated by administering to a subject an agent that binds to an ENaC protein and acts as an agonist or antagonist of ENaC activity.

As used herein, a subject can be any mammal, so long as the mammal is in need of modulation of a pathological or biological process mediated by ENaC. The term "mammal" means an individual belonging to the class Mammalia. The invention is particularly useful in the treatment of human subjects.

As used herein, a biological or pathological process mediated by ENaC refers to the wide variety of cellular events mediated by an ENaC protein. Pathological processes refer to a category of biological processes which produce a deleterious effect. For example, pathological processes mediated by ENaC include PHA 1, hypokalaemic acidosis and salt wasting. These pathological processes can be modulated using agents that reduce or increase the activity of an ENaC protein. Preferably, the agent will act to activate an otherwise inactive altered variant of an ENaC protein.

As used herein, an agent is said to modulate a pathological process when the agent reduces the degree or severity of the pathological process. For example, an agent is said to modulate PHA1 when the agent contributes to normal intra and extracellular sodium concentrations.

L. Administration of Agonists and Antagonists of an ENaC Protein

Agonists and antagonists of the ENaC protein can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. For example, to treat pathological conditions resulting from abnormal ion transport, such as water retention, increased blood pressure, chronic respiratory and metabolic acidosis, inflammation, etc., an agent that modulates ENaC activity is administered systemically or locally to the individual being treated. As described below, there are many methods that can readily be adapted to administer such agents.

The present invention further provides compositions containing an antagonist or agonist of an ENaC protein that is identified by the methods herein described. While individual needs vary, a determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble variant, for example, water-soluble salts. In addition, suspensions of the active compounds and as appropriate, oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension and include, for example, sodium carboxymethyl cellulose, sorbitol, and/or dintran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release variants thereof.

M. Combination Therapy

The agents of the present invention that modulate ENaC activity can be provided alone, or in combination with another agents that modulate a particular biological or pathological process. For example, an agent of the present invention that reduces ENaC activity can be administered in combination with other agents that affect the sodium transport. As used herein, two agents are said to be administered in combination when the two agents are administered simultaneously or are administered independently in a fashion such that the agents will act at the same time.

N. Animal Models and Gene Therapy

The ENaC genes and the ENaC proteins can also serve as targets for gene therapy in a variety of contexts. For example, in one application, ENaC-deficient non-human animals can be generated using standard knock-out procedures to inactivate an ENaC gene or, if such animals are non-viable, inducible ENaC antisense molecules can be used to regulate ENaC activity/expression. Alternatively, an animal can be altered so as to contain an ENaC or antisense-ENaC expression unit that directs the expression of ENaC or the antisense molecule in a tissue specific fashion. In such uses, a non-human mammal, for example a mouse or a rat, is generated in which the expression of the ENaC gene is altered by inactivation or activation. This can be accomplished using a variety of art-known procedures such as targeted recombination. Once generated, the ENaC-deficient animal, the animal that expresses ENaC in a tissue specific manner, or an animal that expresses an antisense molecule can be used to 1) identify biological and pathological processes mediated by ENaC, 2) identify proteins and other genes that interact with ENaC, 3) identify agents that can be exogenously supplied to overcome ENaC deficiency and 4) serve as an appropriate screen for identifying mutations within ENaC that increase or decrease activity.

For example, it is possible to generate transgenic mice expressing the human minigene for ENaC in a tissue specific-fashion and test the effect of over-expression of the protein in cells and tissues that normally do not contain ENaC. This strategy has been successfully used for other proteins, namely bcl-2 (Veis et al. Cell 75:229 (1993)). Such an approach can readily be applied to the ENaC protein and can be used to address the issue of a potential beneficial effect of ENaC in a specific tissue area.

In another embodiment, genetic therapy can be used as a means for modulating an ENaC-mediated biological or pathological processes. For example, it may be desirable to introduce into a subject being treated a genetic expression unit that encodes a modulator of ENaC expression, such as an antisense encoding nucleic acid molecule or an ENaC encoding nucleic acid molecule, or a functional ENaC expression unit. Such modulators can either be constitutively produced or inducible within a cell or specific target cell. This allows a continual or inducible supply of a modulator of ENaC or the protein expression within a subject.

The following examples are intended to illustrate, but not to limit, aspects of the present invention.

EXAMPLE 1

Methods

Genotyping and SSCP

SSCP of all coding exons of α, β, and γENaC was performed using specific primers to amplify exons or exon fragments of exons 150–250 base pairs in length from genomic DNA by PCR as previously described (Shimkets, R. A. et al. Cell 79:407–414 (1994)). Forty-three sets of primers were used (Table 2), based on the cloning and characterization of the intron-exon organization of each genomic locus (McDonald, F. J., et al. Am. J. Physiol. 268:L728–734 (1994); McDonald, F. J., et al. Am. J. Physiol. 268: C1157–C1163 (1995); Lu et al., in preparation). Primers are in introns with the exception of large coding exons in which overlapping primer sets in exons are employed. PCR was performed using specific primers and genomic DNA as template, and products were fractionated on non-denaturing gels as described previously (Simon, D. et al. Nature Genet. 12:24–30 (1996)). Novel SSCP conformers were identified by autoradiography, purified, and subjected to direct DNA sequence analysis as described previously (380. In all cases, DNA sequences were confirmed by sequencing both DNA strands. Genotypes of markers closely linked to α or β-γENaC were determined by polymerase chain reaction using specific primers and genomic DNA as template by standard methods. Markers tightly linked to the β-γENaC locus were genotyped as previously described (Shimkets, R. A. et al. Cell 79:407–414 (1994)). Marker loci linked to αENaC were identified by use of an RFLP detected by hybridizing rat αENaC cDNA to TaqI-cut human genomic DNA. Genotyping of 166 individuals in CEPH kindreds revealed linkage of αENaC to loci D12S314 and D12S93 (lod score of 8.3 for linkage to D12S314 at a recombination fraction of 4%), with a peak multipoint lod score localizing the gene 2 cM telomeric to D12S314. Genomic DNA of subjects from PHA kindreds was prepared from venous blood by standard methods (Bell, G., et al. Proc. Natn. Acad. Sci. USA 78:5759–5763 (1981)).

Construction of rat βENaC37S

Serine was substituted for glycine at residue 37 of rat βENaC cDNA by site-directed mutagenesis using a mutagenic primer and PCR. PCR was performed using rat βENaC cDNA21 as a template, a sense mutagenic primer (CCAACACACACAGCCCCAAAC) (SEQ. ID NO:19) extending from nucleotide 170 to 190 (codons 33–39) of the βENaC cDNA sequence and altering nucleotide 181 from G to A, and a reverse or antisense primer (CTTGACCTTGGAGTACTGGAAG)(SEQ. ID NO:20), extending from nucleotide 378 to 400. After PCR, this product was purified and used as a primer in conjunction with the vector Sp6 primer to direct PCR using the rat βENaC cDNA as a template. The resulting product contained the desired mutation, and was cleaved at a unique EcoRI cleavage site in vector sequence and a unique ScaI site in codon 146. This fragment was purified and substituted for the corresponding wild-type sequence in the βENaC cDNA. The structure and sequence of the resulting mutant construct was confirmed by DNA sequencing.

Expression Studies of Normal and Mutant ENaC

Complementary RNAs (cRNA) of each α, β and γ subunit were synthesized in vitro. Equal saturating concentrations of each subunit cRNA (3 ng total cRNA of each subunit/oocyte) were injected into stage V to VI oocytes as previously described (Schild, L. et al. *Proc. Natn. Acad. Sci. USA* 92:5699–5703 (1995)); cRNAs injected together were normal a, β and γ subunits; normal α and γ subunits plus mutant β subunits; normal α and γ subunits alone with no β subunits. Oocytes from the same frog were injected on the same day with wild-type or mutant constructs. Twenty-four hours after injection, whole-oocyte currents were measured using two-electrode voltage clamp technique in a medium containing: 120 mM NaCl, 2.5 mM KCl, 1.8 mM $CaCl_2$, 10 mM HEPES-NaOH pH 7.2. The expressed ENaC channel activity was assessed by measurement of the amiloride-sensitive Na current, defined as the difference between the Na current recorded at a membrane potential of –100 mV in the absence and presence in the medium of 5 µM amiloride. The results were analyzed by T-test.

Comparable expression-levels of the wild-type β subunit and one containing the G37S mutation in Xenopus oocytes were ensured by immunoprecipitation. Oocytes injected with cRNAs encoding either α, β and γ, or α and γ or α, βG37S and γ subunits were labeled for 14 h with (35S) methionine, and microsomal membranes were prepared. The three subunits were immunoprecipitated under denaturing conditions with specific antisera and immunoprecipitates were separated on a 8% SDS-polyacrylamide gel (Duc, C., et al. *J. Cell. Biol.* 127:1907–1921(1994)).

Results

PHA Kindreds

Seven PHA1 kindreds containing 10 living affected subjects were ascertained in Saudi Arabia and Israel (Table 1). Two of these kindreds, PHA K10, and PHA K3 have been previously reported (Mathew, P. M., et al. *Clinical Pediatrics.* 1:58–60 (1993); Hanukoglu, A. *J. Clin. Endocrin. & Metab.* 73,936–944 (1991)). All affected subjects were the product of consanguineous union, supporting autosomal recessive transmission (FIG. 1). Most subjects were diagnosed in the neonatal period, and all had clinical features of severe dehydration, hypotension, hyponatremia, hyperkalaemia, and metabolic acidosis despite normal glomerular filtration rate. Plasma renin activity and aldosterone concentrations were markedly elevated. No subjects had signs of abnormal virilization. Multi-organ involvement was documented in PHA K3 (Hanukoglu, A. *J. Clin. Endocrin. & Metab.* 73,936–944 (1991)). Several index cases had siblings who died with a similar syndrome in the first days of life (FIG. 1). Clinical management consisted of dietary sodium supplementation and use of an ion binding resin or dialysis to reduce potassium levels. The constellation of clinical features permitted definitive diagnosis of PHA1 in all affected subjects.

Mutations in αENaC in PHA1

The a subunit of ENaC is required for ENaC activity (Canessa, C. M. et al. *Nature* 367:463–467 (1994)), and consequently loss of function mutations in this gene could result in a syndrome similar to PHA1. Affected subjects arising from consanguineous union are expected to be homozygous for the same mutant allele at the trait locus; in contrast, random loci will be homozygous for an ancestral allele with likelihood 1 in 16 in the offspring of 1st cousins and 1 in 64 in the offspring of second cousins, providing a powerful test of linkage (Lander, E. S. et al. *Science* 236:1567–1570 (1987)). Accordingly, the knowledge of the intron-exon structure of αENaC and single-strand conformational polymorphism (SSCP was used) to screen for molecular variants in exons and intron-exon boundaries of this gene in PHA1 patients. Affected subjects in 4 of the 7 kindreds showed novel αENaC variants that in each case were homozygous in all affected subjects in each kindred (FIGS. 2a and 2b); no other missense variants or variants altering consensus splice sites were identified. In each case the parents were heterozygous for these variants and none of the unaffected siblings inherited two copies of the variant, demonstrating cosegregation of these variants with PHA1 in these kindreds (FIGS. 1 and 2).

That these variants are homozygous by descent from a great-grandparent is supported by the finding that these variants are rare (absent in 160 alleles from unrelated subjects who do not have PHA1) and that two highly polymorphic loci tightly linked to αENaC, D12S314 and D12S93 (Gyapay, G. et al. *Nature Genet.* 7:246–339 (1994)), are each homozygous in affected subjects of these kindreds (data not shown).

Figures 2A, 2B:
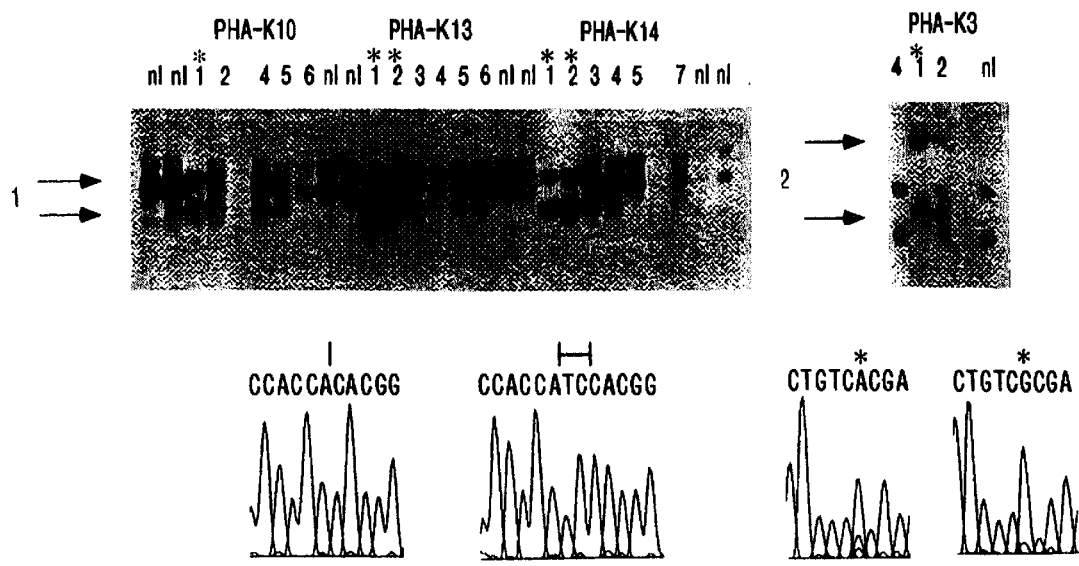

Affected subjects in three of these kindreds, all Saudi natives ascertained in Dhahran but not known to be related to one another, showed indistinguishable homozygous variants in exon 2 of αENaC (FIG. 2a). DNA sequence analysis of the variant in these kindreds revealed a 2 base pair deletion at codon I68, introducing a frameshift mutation (FIG. 2a). This mutation disrupts the encoded protein prior to the first transmembrane domain (FIG. 3a); the encoded protein bears no similarity to the normal protein from amino acid 68 through amino acid 144, where a termination codon ends translation.

Figures 3A, 3B:
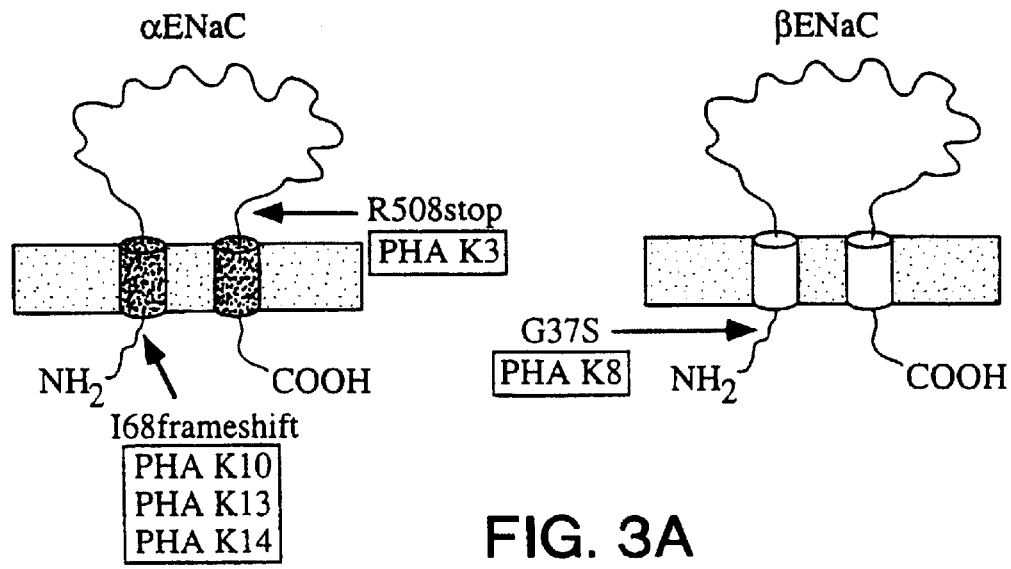

The DNA sequence of the homozygous αENaC variant in the fourth kindred, PHA K3 from Israel, reveals a single base substitution changing codon R508 from CGA to TGA and introducing a premature termination codon (FIG. 2b, FIG. 3a). This codon is in the extracellular domain, and thus results in a protein containing a normal first transmembrane domain, part of the extracellular domain and missing the second transmembrane domain as well as the intracytoplasmic C-terminus.

Both of these mutations result in αENaC subunits that lead to loss of ENaC channel activity since an intact second transmembrane domain is required for normal channel activity (Li, X. J., et al. *Molecular Pharmacology* 47:1133–1140 (1995)). These mutations can thus explain the pathogenesis of PHA1 in these families.

Another mutation in the a subunit of EnaC, which also causes pseudohypoaldosteronism type I, is the mutation of cysteine 133 to tyrosine.

Mutation in βENaC in PHA1

Identification of mutations in αENaC in 4 PHA1 kindreds leaves open the question of whether other kindreds also harbor mutations at this locus, or alternatively whether there might be mutations at other loci that account for the disease in these remaining kindreds. The β and γ subunits of ENaC were tested for mutation by systematic screening of exons of these genes.

Figure 2C:
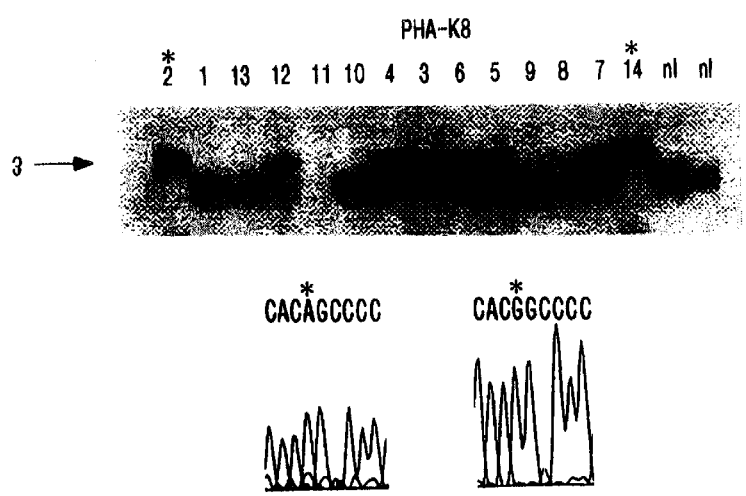

This screening in all PHA1 kindreds revealed a single variant altering the encoded protein in PHA K8 (FIG. 2c). This kindred is particularly informative because two unaffected brothers had affected offspring, one of these via union with a second cousin, the other via a spouse of uncertain relationship (FIG. 1). The affected third cousins are homozygous for the same variant, while none of their unaffected siblings or relatives are homozygous for this variant; moreover, this variant is absent in 160 alleles of unrelated healthy subjects. In addition, genotypes of marker loci tightly linked to bENAC, D16S412, D16S417 and D16S420 are all homozygous in these affected subjects but not their unaffected relatives, strongly supporting the identity by descent of the observed mutation.

DNA sequence analysis reveals that this βENaC variant substitutes serine for glycine at amino acid 37 of βENaC (FIG. 2C, FIG. 3). While the cytoplasmic amino termini of α, β and γ ENaC generally show little amino acid sequence identity with one another, it is noteworthy that G37 is in a segment that shows homology among all members of the extended ENaC family ranging from humans to C. elegans (FIG. 3b) (Canessa, C. M., et al. *Nature* 361:467–470 (1993); Canessa, C. M. et al. *Nature* 367:463–467 (1994); McDonald, F. J., et al. *Am. J. Physiol.* 268:L728–734 (1994); McDonald, F. J., et al. *Am. J. Physiol.* 268:C1157–C1163 (1995); Puoti, A. et al. *Am J. Physiol.* 269:C188–C197 (1995); Waldmann, R., et al. *J. of Biol. Chem.* 270:27411–27414 (1995); Huang, M. et al. *Nature* 367:467–470 (1994); Chalfie, M. et al. *Nature* 345:410–416 (1990)).

The functional significance of the G37S variant was assessed by expression of this βENaC variant in conjunction with normal α and γ subunits in Xenopus oocytes as described previously (Hansson, J. H. et al. *Nature Genetics* 11:76–82 (1995); Hansson, J. H. et al. *Proc. Natn. Acad. Sci. USA* 92:11495–11499 (1995); Schild, L. et al. *Proc. Natn. Acad. Sci. USA* 92:5699–5703 (1995)). The amiloride-sensitive $Na^+$ current, measured by 2-electrode voltage clamp in oocytes expressing the wild-type ENaC, ENaC containing the mutant β subunit, and channels containing only α and γ subunits was determined and compared (FIG. 4). In order to compare levels of ENaC proteins in oocytes expressing wild-type and mutant channels, subunits were immunoprecipitated from oocyte membranes using specific antibodies to each subunit (Duc, C., et al. *J. Cell. Biol.* 127:1907–1921 (1994)). The results demonstrated indistinguishable levels of each subunit in oocytes expressing wild type and mutant ENaC (data not shown). Comparison of $Na^+$ currents in oocytes expressing wild-type or mutant ENaCs demonstrate a highly significant reduction in ENaC activity in oocytes expressing the mutant β subunit (40% of wild-type activity, p<0.00001). Oocytes expressing the mutant β subunit, however, still have significantly higher activity than channels expressing no β subunit (p=0.00001), suggesting that this mutation does not result in complete loss of function.

The strong evidence of cosegregation of βENaC G37S with PHA in this kindred and the loss of function demonstrated on expression indicates the functional significance of this mutation, revealing genetic heterogeneity of PHA1.

Another mutation in the β subunit of ENaC which also causes pseudohypoaldosteronism type I occurs when glycine-37 is mutated to a serine residue.

TABLE 1

Characteristics of index cases of PHA 1 kindreds

| Kindred | Location | Ethnicity | Age | Na + | K + | PAC | Mutation |
|---|---|---|---|---|---|---|---|
| PHA K10 | Saudi Arabia | Saudi | 7 d | 124 | 7.7 | 1.87 | αENaC 168fr |
| PHA K13 | Saudi Arabia | Saudi | 1 d | 126 | 11.2 | 6.28 | αENaC 168fr |
| PHA K14 | Saudi Arabia | Saudi | 8 d | 128 | 10.9 | 15.16 | αENaC 168fr |
| PHA K3 | Israel | Iranian Jew | 9 d | 125 | 10.0 | 14.27 | αENaC R508stop |
| PHA K8 | Israel | Arabic | 19 d | 133 | 8.2 | 1.00 | βENaC G37S |
| PHA K12 | Saudi Arabia | Pakistani | 235 d | 107 | 6.9 | 3.24 | none |
| PHA K7 | Saudi Arabia | Sudanese | 5 d | 112 | 11.0 | 8.64 | none |

Age, age at clinical presentation (days); $Na^+$, serum sodium concentration (mM), normal 138–142; $K^+$ serum potassium concentration (mM), normal 3.5–5.0; PAC, plasma aldosterone concentration (ng dl-1), normal 1–95. fr, frameshift.

TABLE 2

Primers used to amplify coding regions of ENaC subunits

| Primer | Exon | Forward | Reverse |
|---|---|---|---|
| A-1 | 1 | ACCCTTGCTCTCTCCAATCCAC | GAACTCGATCAGGGCCTCCTC |
| A-2 | 2 | CTGCAACAACACCACCATCCAC | GGGGCAGAGGGACTAACCGAC |
| A-3 | 3 | AGCTCCTTCACCACTCTCGTG | GGACCCTCAGGCGCTGCAAG |
| A-4 | 3 | AGCTCCTTCACCACTCTCGTG | GTCAGGAAAGGAGCGGAGCCCATG |
| A-5 | 4 | CCTCTGACTCTAGTCTCTGTGTC | GGAGCCAGGCAGGACTGACTC |
| A-6 | 5 | GACCCTACTCTCTCTTTTCCTG | CGCCATGGAGCAAGCAGGGAG |
| A-7 | 6 | GCCAACTCTGCTCTCTCTGCAC | CCTTCCAGGCCTCCCAGTCAG |
| A-8 | 7 | CACGGAATCAGGTTGGGCCTC | CACGGAATCAGGTTGGGCCTC |
| A-9 | 8 | CCTCTCCACCCTCCTCCCTTC | GGGGCTCCCTGGAGTCTCAC |
| A-10 | 9 | ACAGGCATCTCTCTGTACCCAC | TGGCTCGGTAACCTGTATTCTAC |

TABLE 2-continued

Primers used to amplify coding regions of ENaC subunits

| Primer | Exon | Forward | Reverse |
|---|---|---|---|
| A-11 | 10 | AACACTGAGCACCTTTCTCCATC | ACCCATCCCTTCCCCACACTC |
| A-12 | 11 | GACCTTGATGACACCCCCATTC | CAGGGACCAGGGCAGGACTG |
| A-13 | 12 | TCTTCCCACCCTCTGTCCCAC | CAGGCTCCATCCAGGCACGAC |
| A-14 | 13 | AGAACCCTCTGTCCCATCGTC | CTGGAGACCAGTATCGGCTTC |
| A-15 | 13 | GTCTGTGGTGGAGATGGCTGAG | GCCTGGGTGGGACAAGGACAG |
| A-16 | 13 | GGTAGCCTCCACCCTGGCATC | GCCTTGGTGTGAGAAACCTCTC |
| B-1 | 1 | ATGCCTCTCTGCAGGTGCCAC | AGCTGTGCACTCCGGGGCCAC |
| B-2 | 2 | TTCCCCCTAACCAGCCCTCTC | CATTGCTTGATATGTGCCCAG |
| B-3 | 3 | TGGCCTCCACAGTGTAGCCTC | CATCTCTACTAGCTCCTGCTG |
| B-4 | 3 | TGGCCTCCACAGTGTAGCCTC | CCGACTGTCCGTAGGTGCCAG |
| B-5 | 4 | CCTGCCCTGCAGCTGATGCTG | GGTTAAAGCCTCATGGCTCTG |
| B-6 | 5 | CGCAGCCCTCACCCCACCCTC | GCCCTTGGGCTCCGGCCATAC |
| B-7 | 6 | AAGCAACCCCTCTAAACACAG | AGGCGTGCACCACCTTCCCAC |
| B-8 | 7 | CCTGTGTTCTCTCATTATGAAC | GATCCCCCGTGCCCCCGCTC |
| B-9 | 8 | AACCTCTTGGCCGCCTTTCTG | TGTGCCCGCCCACCCGCACTC |
| B-10 | 9 | GCAGGGACCACAACAGGCCTG | GTGGTTGCAAAAGTTGCCATC |
| B-11 | 10 | GATGGCAACTTTTGCAACCAC | CCAGCCCCGCCCAGGCTCAG |
| B-12 | 11 | GGCCCATCTCGCTGCCTCCTG | AGGGCTGGGGTATTGGGAGAC |
| B-13 | 12 | CAAGAATGTGTGGCCTGAG | AAAGTTGGTGTGGGCCTCCAC |
| B-14 | 12 | CACCAACTTTGGCTTCCAGCC | GGCTGCTCAGTGAGTTTCAG |
| B-15 | 12 | CTGGTGGCCTTGGCCAAGAG | GTCCAGCGTCTGCAGACGCAG |
| G-1 | 1 | GTCCCATCCTCGCCATG | CTGCAACATCAACCCCTACAA |
| G-2 | 2 | CCCTCTCCCTGACTTTTCCTC | AATGAGAAGGTGAAATCTTACC |
| G-3 | 3 | CGCATCTCCTCTTATTCACAG | AGAGCAGCATTCTCTCCTGAC |
| G-4 | 4 | GACCCATTTTCTTCCTCCATAG | CCTTGGCACAGGTTTCCTTAC |
| G-5 | 5 | CAGGTGGTCTTATCCTCCCAG | CTCCAAGCCTATGGAAATGAG |
| G-6 | 6 | GAGGACAGGGCTGAGTGTGTG | CAGGGCTGGGTGCCCCTGCCA |
| G-7 | 7 | TCCTGGGTCTCCTCTTTCAGA | CTGGAGCTGGGTCTCACTCAC |
| G-8 | 8 | GCCCTCTCCCTTGTCCCTCAG | GTTCCCCACTCTGCCCACCG |
| G-9 | 9 | CGCTTTCTCTCTCCGTTGTAG | GAACAGGGTAGAGGTAACTTAC |
| G-10 | 10 | TTCACCTGTTGGAATTTTGCAG | GAAGGAAGCCACTCTACTCAC |
| G-11 | 11 | TTGATGGTGTGGCTTGGCCTG | TACGGGGAGCTTCTGGACATG |
| G-12 | 11 | GCAGAAAGCCAAGGAGTGGTG | GATCTGTCTTCTCAACCCTGC |

Primers are all presented 5'-3'. A, B, and G refer to primers for αENaC, βENaC and γENaC, respectively. Primers A13R, A14F, B13R, B14F and R, B15F, G1F and R, G11R and G12F are in coding regions; the remainder are in introns or untranslated regions. Forward primers A-1 through A-16 correspond to SEQ ID NO: 21 through SEQ ID NO: 36, respectively. Reverse primers A-1 through A-16 correspond to SEQ ID NO: 37 through SEQ ID NO: 52, respectively. Forward primers B-1 through B-15 correspond to SEQ ID NO: 53 through SEQ ID NO: 67, respectively. Reverse primers B-1 through B-15 correspond to SEQ ID NO: 68 through SEQ ID NO: 82, respectively. Forward primers G-1 through G-12 correspond to SEQ ID NO: 83 through SEQ ID NO: 94, respectively. Reverse primers G-1 through G-12 correspond to SEQ ID NO: 95 through SEQ ID NO: 106, respectively.

Discussion

The finding of independent mutations in ENaC subunits that cosegregate with PHA 1, are homozygous by descent in affected offspring of consanguineous union, and result in diminished ENaC activity constitute proof that mutations in subunits of the epithelial sodium channel cause autosomal recessive PHA1.

Thus far, functional mutations in 5 of 7 consanguineous kindreds studied have been identified; these mutations occur in either the α or β subunits of ENaC, demonstrating genetic heterogeneity of the trait. In the two kindreds in which mutations have not thus far been identified, one case is homozygous for all markers tightly linked to the β-γ ENaC locus, raising the possibility of an undetected mutation; the other case is not homozygous for any loci linked to β-γ ENaC, and is homozygous for only one of two loci tested linked to αENaC. This latter subject presented at 8 months of age (Table 1), later than typical PHA1 subjects, raising the possibility that this patient might have a somewhat different clinical syndrome. These findings leave open the question of whether additional loci will prove to contribute to the pathogenesis of recessive forms of PHA 1.

In contrast to the recessive kindreds described here, some PHA1 kindreds have been reported to show autosomal dominant transmission (Hanukoglu, A. *J. Clin. Endocrin. & Metab.* 73,936–944 (1991); Limal, J. M., et al. Lancet 1:51 (1978); Hanukoglu, A., et al. *Lancet* 1:1359 (1978)). Since ENaC is a multimeric channel, it is possible that some ENaC mutations could have dominant negative function, with one defective gene product sufficient to disrupt normal assembly of a large fraction of channels. Further investigation of such kindreds will be required to evaluate this possibility.

Knowledge that PHA1 can result from loss of function mutations in ENaC provides the basis for a detailed understanding the pathogenesis of this disease. Affected neonates have a primary defect in renal sodium reabsorption mediated via this channel. The consequence is salt wasting, leading to intravascular volume depletion; this results in a marked increase in secretion of renin and consequently aldosterone, in an effort to restore plasma volume. However, because ENaC is defective, renal sodium reabsorption cannot be appropriately increased, resulting in persistent intravascular volume depletion. In addition, sodium reabsorption via ENaC is indirectly coupled to $K^+$ secretion and $H^+$ secretion in the distal nephron. As a result, the loss of ENaC function impairs the ability to secrete K⁺ and H⁺, contributing to hyperkalaemia and metabolic acidosis; these features are further worsened by poor perfusion of tissues due to hypovolemia. In addition to this renal defect, parallel defects altering ENaC function in the colon and sweat glands may further augment salt wasting.

One puzzling clinical feature of PHA1 has been the observation that some affected children "grow out" of the disease, meaning that at older ages they can stop supplemental dietary salt. It has been proposed that such patients usually if not always have autosomal dominant disease (Hanukoglu, A. *J. Clin. Endocrin. & Metab.* 73,936–944 (1991)). Consistent with this distinction, the subjects reported here all show recessive transmission and all remain dependent on supplemental dietary salt. It will consequently be of interest to determine whether kindreds showing clear-cut dominant transmission or cases with sporadic disease who improve with age harbor mutations in ENaC subunits.

It has recently been appreciated that ENaC plays a major role in the removal of salt and water from the alveolar space in the lung (Strang, L. B. *Physiol. Rev.* 71:991–1016 (1991)). This finding has been emphasized by an αENaC knock-out mouse that shows neonatal lethality due to respiratory failure, apparently from an inability to clear fluid from the alveolar space (Hummler et al. *Nature Genet.* 1996 (In Press)). It consequently is of interest that some PHA 1 patients have concurrent respiratory problems (Hanukoglu, A., et al. *J. Pediatr.* 125: 752–755 (1994)); interestingly, patient PHA K3-1, who has a truncated αENaC, has a history of recurrent respiratory infections. Nonetheless, these patients do not have a clinical picture of acute respiratory distress syndrome (ARDS), raising the question of whether the αENaC mutations result in complete knock-outs of ENaC activity or whether the portion of αENaC expressed in these patients is sufficient to provide some residual ENaC function in vivo, for example by permitting assembly or targeting of other subunits to the apical membrane. Further investigation of these channels and the pulmonary manifestations in these patients will consequently be of interest.

Identification of the molecular basis of this disease provides the means for prenatal genetic testing, which may prove to be of clinical benefit in preventing early death from this disease in kindreds known to be segregating this trait. Affected subjects in all 3 native Saudi PHA1 kindreds are homozygous for the identical variant, almost certainly by descent from a remote common ancestor. Since these kindreds are not known to be related to one another, this finding suggests that this mutation will prove to be a predominant cause of PHA1 in this country.

These findings bring the number of genes in which mutation causes primary renal salt wasting in humans to 3- the two genes identified herein, and mutations in the thiazide-sensitive sodium-chloride cotransporter that cause Gitelman's syndrome (Simon, D. et al *Nature Genet.* 12:24–30 (1996)), a disorder characterized by primary renal tubular salt wasting in association with hypokalaemic metabolic alkalosis. These findings underscore the primary role of the kidney in regulating intravascular volume and controlling the ionic composition of the vascular space.

Finally, it is noteworthy that mutations in ENaC subunits cause two diseases: loss of function mutations cause salt wasting and PHA1, while gain of function mutations cause hypertension and Liddle syndrome. That extreme variation in ENaC activity either augments or reduces sodium reabsorption and blood pressure in humans motivates the further examination of these genes and their regulators in the pathogenesis of human blood pressure variation. The variants listed below, which occur in either the α, β, γ subunits of ENaC, have been obtained from patients suffering from hypertension.

In the α Subunit of ENaC:
  Alanine 334 to threonine
  Tryptophan 493 to arginine
  Cysteine 618 to phenylalanine
In the β Subunit of ENaC:
  Serine 82 to cysteine
  Alanine 567 to valine
  Isoleucine 586 to histidine
  Glycine 589 to serine
  Threonine 594 to methionine
  Alanine 595 to aspartate
  Arginine 625 to cysteine
  valine 630 to isoleucine
In the γ Subunit of ENaC:
  Threonine 259 to asparagine
  Serine 373 to asparagine
  Valine 443 to leucine
  Proline 502 to alanine
  Lysine 570 to asparagine The functional significance of these mutations has been assessed in vitro by expression in Xenopus laevis oocytes. The tryptophan 493 to arginine variant in the α subunit causes marked activation of sodium transport, suggesting a functional role in vivo.

A skilled artisan can readily practice the inventions disclosed herein following the methods and Examples provided herein.

What is claimed is:

1. A method for identifying a carrier of psuedohypoaldosteronism type-1 (PHA-1), comprising the steps of:
   a) isolating a nucleic acid sample from an individual; and
   b) analyzing the nucleic acid sample for the presence or absence of a nucleic acid comprising the nucleotide sequence of SEQ ID NO: 2, 4, or 6, whereby the presence of any one of the nucleotide sequences is indicative of a PHA-1 carrier.

2. The method of claim 1, further comprising amplification of the isolated nucleic acid of step (a), wherein the amplification product is analyzed in step (b).

3. The method of claim 2, wherein the amplification in step (a) comprises use of a polymerase chain reaction (PCR).

4. The method of claim 1, wherein the isolated nucleic acid is analyzed by nucleotide sequencing, selective nucleic acid hybridization, oligonucleotide ligation, RNase mismatch cleavage, restriction fragment polymorphism, allele-specific PCR, single strand conformation polymorphism, electrophoresis, or combinations thereof.

5. The method of claim 2, wherein the amplification product is analyzed by nucleotide sequencing, selective nucleic acid hybridization, oligonucleotide ligation, RNase mismatch cleavage, restriction fragment polymorphism, allele-specific PCR, single strand conformation polymorphism, electrophoresis, or combinations thereof.

6. A method for identifying a carrier of pseudohypoaldosteronism type-1 (PHA-1), comprising the steps of:
   a) isolating a nucleic acid sample from an individual; and
   b) analyzing the nucleic acid sample for the presence or absence of a homozygous alteration in the nucleotide sequence of SEQ ID NO:2, 4, or 6, whereby the presence of the homozygous alteration is indicative of a PHA-1 carrier.

* * * * *

UNITED STATES PATENT AND TRADEMARK OFFICE
CERTIFICATE OF CORRECTION

PATENT NO. : 6,551,775 B1  Page 1 of 1
DATED : April 22, 2003
INVENTOR(S) : Richard P. Lifton et al.

It is certified that error appears in the above-identified patent and that said Letters Patent is hereby corrected as shown below:

<u>Column 1,</u>
Line 10, before "TECHNICAL FIELD," please add the following paragraph:

-- STATEMENT REGARDING FEDERALLY SPONSORED RESEARCH OR DEVELOPMENT

This research was supported, in part, by U.S. Government funds (National Institutes of Health Grant No. 5P50HL055007-08), and the U.S. Government may therefore have certain rights in the invention. --

Signed and Sealed this

Fifteenth Day of July, 2003

JAMES E. ROGAN
*Director of the United States Patent and Trademark Office*